(12) United States Patent
Hellerstein et al.

(10) Patent No.: US 9,737,260 B2
(45) Date of Patent: Aug. 22, 2017

(54) METHODS FOR DETERMINING TOTAL BODY SKELETAL MUSCLE MASS

(71) Applicants: GLAXOSMITHKLINE LLC, Wilmington, DE (US); THE REGENTS OF THE UNIVERSITY OF CALIFORNIA, Oakland, CA (US)

(72) Inventors: Marc K. Hellerstein, Kensington, CA (US); William Evans, Emeryville, CA (US)

(73) Assignees: GLAXOSMITHKLINE LLC, Wilmington, DE (US); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/098,217

(22) Filed: Apr. 13, 2016

(65) Prior Publication Data

US 2016/0220182 A1    Aug. 4, 2016

Related U.S. Application Data

(63) Continuation of application No. 14/363,779, filed as application No. PCT/US2012/068068 on Dec. 6, 2012, now abandoned.

(60) Provisional application No. 61/708,013, filed on Sep. 30, 2012, provisional application No. 61/567,952, filed on Dec. 7, 2011.

(51) Int. Cl.
| | |
|---|---|
| *G01N 33/70* | (2006.01) |
| *G01N 33/48* | (2006.01) |
| *A61B 10/00* | (2006.01) |
| *A61B 5/00* | (2006.01) |
| *H01J 49/00* | (2006.01) |
| *A61B 5/107* | (2006.01) |
| *G01N 30/72* | (2006.01) |
| *A61B 5/15* | (2006.01) |
| *G01N 33/493* | (2006.01) |

(52) U.S. Cl.
CPC .......... *A61B 5/4869* (2013.01); *A61B 5/107* (2013.01); *A61B 5/15* (2013.01); *A61B 5/4519* (2013.01); *A61B 10/007* (2013.01); *G01N 30/7233* (2013.01); *G01N 33/70* (2013.01); *H01J 49/004* (2013.01); *H01J 49/0036* (2013.01); *G01N 33/493* (2013.01)

(58) Field of Classification Search
CPC ......... A61B 5/107; A61B 5/15; A61B 5/4519; A61B 5/4869; A61B 10/007; G01N 30/72; G01N 30/7233; G01N 33/48; G01N 33/487; G01N 33/49; G01N 33/493; G01N 33/70; Y10T 436/14; Y10T 436/147777; Y10T 436/24; H01J 49/0036; H01J 49/004

USPC ..... 436/63, 91, 98, 161, 173, 106, 111, 127, 436/128; 422/70; 435/29; 250/282; 600/368

See application file for complete search history.

(56) References Cited

U.S. PATENT DOCUMENTS

| | | |
|---|---|---|
| 4,065,552 A | 12/1977 | Costa |
| 4,332,784 A | 6/1982 | Smith et al. |
| 4,889,126 A | 12/1989 | Doddrell et al. |
| 4,940,658 A | 7/1990 | Allen et al. |
| 5,026,909 A | 6/1991 | Zoltarev et al. |
| 5,042,488 A | 8/1991 | Ackerman |
| 5,167,948 A | 12/1992 | Wenzel |
| 5,209,919 A | 5/1993 | Turteltaub et al. |
| 5,317,098 A | 5/1994 | Shizuya et al. |
| 5,338,686 A | 8/1994 | Hellerstein |
| 5,354,662 A | 10/1994 | Stone et al. |
| 5,376,355 A | 12/1994 | Turteltaub et al. |
| 5,394,236 A | 2/1995 | Murnick |
| 5,432,058 A | 7/1995 | Lange et al. |
| 5,439,803 A | 8/1995 | Ross et al. |
| 5,506,147 A | 4/1996 | Kolhouse et al. |
| 5,597,548 A | 1/1997 | Sherry et al. |
| 5,628,328 A | 5/1997 | Nissen et al. |
| 5,665,377 A | 9/1997 | Gonella |
| 5,665,562 A | 9/1997 | Cook |
| 5,783,445 A | 7/1998 | Murnick |
| 5,855,921 A | 1/1999 | Somlyai |
| 5,910,403 A | 6/1999 | Hellerstein |
| 5,916,537 A | 6/1999 | Kajiwara et al. |
| 5,922,554 A | 7/1999 | Fielding et al. |

(Continued)

FOREIGN PATENT DOCUMENTS

| | | |
|---|---|---|
| AU | 2002365268 B2 | 9/2003 |
| CA | 2464474 A1 | 7/2003 |

(Continued)

OTHER PUBLICATIONS

Clark et al. Journal of Applied Physiology, vol. 116, Apr. 24, 2014, pp. 1605-1613.*

(Continued)

*Primary Examiner* — Maureen Wallenhorst
(74) *Attorney, Agent, or Firm* — Morrison & Foerster LLP

(57) ABSTRACT

The present invention is based on the finding that enrichment of D3-creatinine in a urine sample following oral administration of a single defined dose of D3-creatine can be used to calculate total-body creatine pool size and total body skeletal muscle mass in a subject. The invention further encompasses methods for detecting creatinine and D3-creatinine in a single sample. The methods of the invention find use, inter alia, in diagnosing disorders related to skeletal muscle mass, and in screening potential therapeutic agents to determine their effects on muscle mass.

11 Claims, 6 Drawing Sheets

(56) References Cited

U.S. PATENT DOCUMENTS

| | | |
|---|---|---|
| 5,924,995 A | 7/1999 | Klein et al. |
| 5,961,470 A | 10/1999 | Wagner et al. |
| 6,010,846 A | 1/2000 | Hellerstein |
| 6,031,228 A | 2/2000 | Abramson |
| 6,071,245 A | 6/2000 | Kohno et al. |
| 6,117,656 A | 9/2000 | Seed |
| 6,284,219 B1 | 9/2001 | Ajami |
| 6,306,660 B1 | 10/2001 | Messenger et al. |
| 6,329,208 B1 | 12/2001 | Jones et al. |
| 6,355,416 B1 | 3/2002 | Abramson |
| 6,391,649 B1 | 5/2002 | Chait et al. |
| 6,461,806 B1 | 10/2002 | Hellerstein |
| 6,461,870 B2 | 10/2002 | Yatscoff et al. |
| 6,468,802 B1 | 10/2002 | Yatscoff et al. |
| 6,566,086 B1 | 5/2003 | Al Athel et al. |
| 6,599,750 B2 | 7/2003 | Yatscoff et al. |
| 6,602,715 B2 | 8/2003 | Yatscoff et al. |
| 6,610,270 B1 | 8/2003 | Ajami |
| 6,625,547 B1 | 9/2003 | Korzekwa et al. |
| 6,642,059 B2 | 11/2003 | Chait et al. |
| 6,653,076 B1 | 11/2003 | Franza, Jr. et al. |
| 6,653,090 B1 | 11/2003 | Lopaschuk |
| 6,670,194 B1 | 12/2003 | Aebersold et al. |
| 6,680,203 B2 | 1/2004 | Dasseux et al. |
| 6,764,817 B1 | 7/2004 | Schneider |
| 6,783,751 B2 | 8/2004 | Heumann |
| 6,808,875 B2 | 10/2004 | Hellerstein |
| 6,835,927 B2 | 12/2004 | Becker et al. |
| 6,849,396 B2 | 2/2005 | Schneider |
| 6,872,575 B2 | 3/2005 | Regnier |
| 6,887,712 B1 | 5/2005 | Medford et al. |
| 6,902,719 B2 | 6/2005 | Wagner |
| 6,906,320 B2 | 6/2005 | Sachs et al. |
| 7,001,587 B2 | 2/2006 | Hellerstein |
| 7,022,834 B2 | 4/2006 | Hellerstein |
| 7,048,907 B2 | 5/2006 | Groman et al. |
| 7,057,168 B2 | 6/2006 | Miller et al. |
| 7,084,396 B2 | 8/2006 | Schneider |
| 7,255,850 B2 | 8/2007 | Hellerstein |
| 7,256,047 B2 | 8/2007 | Malloy et al. |
| 7,262,020 B2 | 8/2007 | Hellerstein |
| 7,307,059 B2 | 12/2007 | Hellerstein |
| 7,357,913 B2 | 4/2008 | Hellerstein |
| 7,410,633 B2 | 8/2008 | Hellerstein |
| 7,449,171 B2 | 11/2008 | Hellerstein |
| 7,504,233 B2 | 3/2009 | Hellerstein |
| 7,873,198 B2 | 1/2011 | Shepherd et al. |
| 7,910,323 B2 | 3/2011 | Hellerstein |
| 8,005,623 B2 | 8/2011 | Hellerstein |
| 8,021,644 B2 | 9/2011 | Hellerstein |
| 8,084,016 B2 | 12/2011 | Hellerstein |
| 8,129,335 B2 | 3/2012 | Hellerstein |
| 8,401,800 B2 | 3/2013 | Hellerstein |
| 8,481,478 B2 | 7/2013 | Hellerstein |
| 8,574,543 B2 | 11/2013 | Lee et al. |
| 8,663,602 B2 | 3/2014 | Hellerstein |
| 8,741,589 B2 | 6/2014 | Hellerstein |
| 8,849,581 B2 | 9/2014 | Hellerstein |
| 8,969,287 B2 | 3/2015 | Hellerstein |
| 9,037,417 B2 | 5/2015 | Hellerstein |
| 9,043,159 B2 | 5/2015 | Hellerstein |
| 9,134,319 B2 | 9/2015 | Hellerstein et al. |
| 2003/0068634 A1 | 4/2003 | Hellerstein |
| 2003/0119069 A1 | 6/2003 | Schneider et al. |
| 2003/0133871 A1 | 7/2003 | Hellerstein |
| 2003/0148533 A1 | 8/2003 | Malloy et al. |
| 2003/0180710 A1 | 9/2003 | Lee et al. |
| 2003/0180800 A1 | 9/2003 | Lee et al. |
| 2003/0211036 A1 | 11/2003 | Degani et al. |
| 2003/0224420 A1 | 12/2003 | Hellerstein et al. |
| 2003/0228259 A1 | 12/2003 | Hellerstein |
| 2004/0081994 A1 | 4/2004 | Hellerstein |
| 2004/0091943 A1 | 5/2004 | Schneider |
| 2004/0115131 A1 | 6/2004 | Hellerstein |
| 2004/0121305 A1 | 6/2004 | Wiegand et al. |
| 2004/0152994 A1 | 8/2004 | Meier-Augenstein |
| 2004/0191916 A1 | 9/2004 | Gross et al. |
| 2004/0253647 A1 | 12/2004 | Mathews et al. |
| 2005/0003375 A1 | 1/2005 | Franza et al. |
| 2005/0014181 A1 | 1/2005 | Galis et al. |
| 2005/0019251 A1 | 1/2005 | Hellerstein |
| 2005/0092910 A1 | 5/2005 | Geromanos et al. |
| 2005/0118724 A1 | 6/2005 | Bateman et al. |
| 2005/0147558 A1 | 7/2005 | Hellerstein |
| 2005/0153346 A1 | 7/2005 | Schneider |
| 2005/0175982 A1 | 8/2005 | Iwatani et al. |
| 2005/0180949 A1 | 8/2005 | Emtage et al. |
| 2005/0201937 A1 | 9/2005 | Hellerstein |
| 2005/0202406 A1 | 9/2005 | Hellerstein |
| 2005/0221278 A1 | 10/2005 | Iwatani et al. |
| 2005/0238577 A1 | 10/2005 | Hellerstein |
| 2005/0238581 A1 | 10/2005 | Kurland et al. |
| 2005/0255509 A1 | 11/2005 | Hellerstein et al. |
| 2005/0281745 A1 | 12/2005 | Lee et al. |
| 2006/0008796 A1 | 1/2006 | Hellerstein |
| 2006/0029549 A1 | 2/2006 | Hellerstein |
| 2006/0094057 A1 | 5/2006 | Hellerstein |
| 2006/0100903 A1 | 5/2006 | Lee et al. |
| 2006/0105322 A1 | 5/2006 | Iwatani et al. |
| 2006/0105339 A1 | 5/2006 | Hellerstein |
| 2006/0120961 A1 | 6/2006 | Schneider et al. |
| 2006/0204439 A1 | 9/2006 | Hellerstein |
| 2006/0251576 A1 | 11/2006 | Hellerstein |
| 2006/0280682 A1 | 12/2006 | Hellerstein |
| 2006/0281188 A1 | 12/2006 | Mann et al. |
| 2007/0248540 A1 | 10/2007 | Hellerstein |
| 2008/0003179 A1 | 1/2008 | Hellerstein |
| 2008/0128608 A1 | 6/2008 | Northen et al. |
| 2009/0041661 A1 | 2/2009 | Hellerstein |
| 2009/0042741 A1 | 2/2009 | Northen et al. |
| 2009/0087913 A1 | 4/2009 | Sakuma |
| 2010/0056392 A1 | 3/2010 | Greving et al. |
| 2010/0099891 A1 | 4/2010 | Okuno et al. |
| 2010/0317541 A1 | 12/2010 | Addington et al. |
| 2011/0195865 A1 | 8/2011 | Hellerstein |
| 2014/0005074 A1 | 1/2014 | Hellerstein |
| 2014/0162900 A1 | 6/2014 | Hellerstein |
| 2014/0186838 A1 | 7/2014 | Hellerstein |
| 2014/0193828 A1 | 7/2014 | Hellerstein |
| 2014/0273044 A1 | 9/2014 | Hellerstein |
| 2014/0287957 A1 | 9/2014 | Prusiner et al. |
| 2014/0295484 A1 | 10/2014 | Hellerstein |
| 2014/0295485 A1 | 10/2014 | Hellerstein |
| 2014/0329274 A1 | 11/2014 | Bowen et al. |
| 2014/0353486 A1 | 12/2014 | Leonard |
| 2015/0233938 A1 | 8/2015 | Hellerstein |

FOREIGN PATENT DOCUMENTS

| | | |
|---|---|---|
| CA | 2494715 A1 | 2/2004 |
| CA | 2530789 A1 | 4/2005 |
| CA | 2840691 A1 | 4/2005 |
| CA | 2858368 A1 | 6/2013 |
| EP | 0826377 B1 | 11/2002 |
| EP | 1437966 A1 | 7/2004 |
| EP | 1663319 A2 | 6/2006 |
| EP | 2753707 A1 | 7/2014 |
| EP | 2788772 A1 | 10/2014 |
| JP | 2001-211782 A | 8/2001 |
| JP | 2003-502016 A | 1/2003 |
| JP | 2003-79270 A | 3/2003 |
| JP | 2005-539069 A | 12/2005 |
| JP | 2005-539199 A | 12/2005 |
| JP | 2014-526685 A | 10/2014 |
| SU | 968036 A1 | 10/1982 |
| WO | 90/11371 A1 | 10/1990 |
| WO | 93/20800 A1 | 10/1993 |
| WO | 93/25705 A1 | 12/1993 |
| WO | 95/13096 A1 | 5/1995 |
| WO | 98/51820 A1 | 11/1998 |
| WO | 00/12535 A2 | 3/2000 |
| WO | 00/13025 A1 | 3/2000 |
| WO | 00/55355 A2 | 9/2000 |
| WO | 00/63683 A1 | 10/2000 |

(56) References Cited

FOREIGN PATENT DOCUMENTS

| | | | |
|---|---|---|---|
| WO | 01/80715 A2 | 11/2001 | |
| WO | 01/84143 A1 | 11/2001 | |
| WO | 03/034024 A2 | 4/2003 | |
| WO | 03/061479 A1 | 7/2003 | |
| WO | 03/068919 A2 | 8/2003 | |
| WO | 03/087314 A2 | 10/2003 | |
| WO | 2004/003493 A2 | 1/2004 | |
| WO | 2004/011426 A2 | 2/2004 | |
| WO | 2004/016156 A2 | 2/2004 | |
| WO | 2004/021863 A2 | 3/2004 | |
| WO | 2004/024941 A2 | 3/2004 | |
| WO | 2004/025270 A2 | 3/2004 | |
| WO | 2004/042360 A2 | 5/2004 | |
| WO | 2004/016156 A3 | 6/2004 | |
| WO | 2005/009597 A2 | 2/2005 | |
| WO | 2005/015155 A2 | 2/2005 | |
| WO | 2005/033652 A2 | 4/2005 | |
| WO | 2005/051434 A1 | 6/2005 | |
| WO | 2005/087943 A1 | 9/2005 | |
| WO | 2006/050130 A2 | 5/2006 | |
| WO | 2006/081521 A2 | 8/2006 | |
| WO | 2006/107814 A2 | 10/2006 | |
| WO | 2010/012306 A1 | 2/2010 | |
| WO | 2010/136455 A1 | 12/2010 | |
| WO | 2010/144876 A1 | 12/2010 | |
| WO | 2011/004009 A1 | 1/2011 | |
| WO | 2011/160045 A1 | 12/2011 | |
| WO | 2013/036885 A1 | 3/2013 | |
| WO | 2013/086070 A1 | 6/2013 | |
| WO | 2014/201291 A1 | 12/2014 | |

OTHER PUBLICATIONS

Stimpson et al. Journal of Applied Physiology, vol. 112, Mar. 15, 2012, pp. 1940-1948.*
MacNeil et al. Journal of Chromatography B, vol. 827, 2005, pp. 210-215.*
Abou-Donia et al., "Mechanisms of Joint Neurotoxicity of n-Hexane, Methyl Isobutyl Ketone and O-Ethyl 0-4-Nitrophenyl Phenylphosphonothioate in Hens", The Journal of Pharmacology and Experimental Therapeutics, vol. 257, No. 1, 1991, pp. 282-289.
Abramson, Hanley N., "The Lipogenesis Pathway as a Cancer Target", Journal of medicinal chemistry, vol. 54, 2011, pp. 5615-5638.
Abu-Qare et al., "Quantification of Nicotine, Chlorpyrifos and Their Metabolites in Rat Plasma and Urine Using High-Performance Liquid Chromatography", Journal of Chromatography B., vol. 757, 2001, pp. 295-300.
Ackermans et al., "The Quantification of Gluconeogenesis in Healthy Men by 2H2O and [2-13C]Glycerol Yields Different Results: Rates of Gluconeogenesis in Healthy Men Measured with 2H2O are Higher than those Measured with [2-13C]Glycerol", The Journal of Clinical Endocrinology & Metabolism, vol. 86, No. 5, 2001, pp. 2220-2226.
Ackerstaff et al., "Choline Phospholipid Metabolism: A Target in Cancer Cells?", Journal of cellular biochemistry, vol. 90, 2003, pp. 525-533.
Adami et al., "The Aetiology and Pathogenesis of Human Breast Cancer", Mutation Research, vol. 333, 1995, pp. 29-35.
Ahmad et al., "Systematic Analysis of Protein Pools, Isoforms, and Modifications Affecting Turnover and Subcellular Localization", Molecular & Cellular Proteomics, vol. 11, No. 3, Mar. 2012, pp. 1-15.
Airhart et al., "Compartmentation of Free Amino Acids for Protein Synthesis in Rat Liver", The Biochemical Journal, vol. 140, 1974, pp. 539-545.
Ajie et al., "In Vivo Study of the Biosynthesis of Long-Chain Fatty Acids Using Deuterated Water", The American Journal of Physiology, vol. 269, 1995, pp. E247-E252.
Anderson et al., "Direct HIV Cytopathicity cannot Account for CD4 Decline in AIDS in the Presence of Homeostasis: A Worst-Case Dynamic Analysis", Journal of Acquired Immune Deficiency Syndromes and Human Retrovirology, vol. 17, 1998, pp. 245-252.
Antelo et al., "Adipose Triglyceride (TG) Turnover and De Novo Lipogenesis (DNL) in Humans: Measurement by Long-Term 2H20 Labeling and Mass Isotopomer Distribution Analysis (MIDA)", Experimental Biology, FASEB# 361.10, 2002, p. A400 (Abstract only).
Asher et al., "Evaluation of Cell Death in EBV-Transformed Lymphocytes Using Agarose Gel Electrophoresis, Light Microscopy and Electron Microscopy. II. Induction of Non-Classic Apoptosis ("Para-Apoptosis") by Tritiated Thymidine", Leukemia & Lymphoma, vol. 19, 1995, pp. 107-119.
Attardi et al., "Biogenesis of Mitochondria", Annual Review of Cell Biology, vol. 4, 1988, pp. 289-333.
Australian Patent Office Search Report mailed Aug. 26, 2005, for Singapore patent application No. SG 200500571-5, filed Jul. 25, 2003, 5 pages.
Australian Search Report and Written Opinion mailed Aug. 5, 2009, for Singapore Application No. 200717391-7 filed May 3, 2006, 7 pages.
Aydemir et al., "Effects of Defibrotide on Aorta and Brain Malondialdehyde and Antioxidants in Cholesterol-Induced Atherosclerotic Rabbits", International Journal of Clinical & Laboratory Research, vol. 30, 2000, pp. 101-107.
Bach et al., "Stem Cells: The Intestinal Stem Cell as a Paradigm", Carcinogenesis, vol. 21, No. 3, 2000, pp. 469-476.
Backhouse et al., "Effects of Haloperidol on Cell Proliferation in the Early Postnatal Rat Brain", Neuropathology and Applied Neurobiology, vol. 8, No. 2, 1982, pp. 109-116.
Bandsma et al., "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile", The Biochemical Journal, vol. 329, 1998, pp. 699-703.
Bandsma et al., "The Contribution of Newly Synthesized Cholesterol to Bile Salt Synthesis in Rats Quantified by Mass Isotopomer Distribution Analysis", Biochemica et Biophysica Acta, vol. 1483, 2000, pp. 343-351.
Bantscheff et al., "Quantitative Mass Spectrometry in Proteomics: A Critical Review", Anal Bioanal Chem., vol. 389, 2007, pp. 1017-1031.
Baran et al., "Mass Spectrometry based Metabolomics and Enzymatic Assays for Functional Genomics", Current Opinion in Microbiology, vol. 12, No. 5, 2009, pp. 547-552.
Bartella et al., "Proton MR Spectroscopy with Choline Peak as Malignancy Marker Improves Positive Predictive Value for Breast Cancer Diagnosis: Preliminary Study", Radiology, vol. 239, No. 3, Jun. 2006, pp. 686-692.
Bertani et al., "Measurement of Total Body Water (TBW) Through In Vivo Dilution of Tracer Compounds: Use of D2O and its Determination by FT Infrared Spectroscopy", Annali Di Chimica, vol. 92, 2002, pp. 135-138.
Bertos et al., "Breast Cancer—One Term, Many Entities?", The Journal of Clinical Investigation, vol. 121, No. 10, Oct. 3, 2011, pp. 3789-3796.
Bickenbach, J. R., "Identification and Behavior of Label-Retaining Cells in Oral Mucosa and Skin", Journal of Dental Research, 1981, pp. 1611-1620.
Bier, D. M., "Stable Isotopes in Biosciences, their Measurement and Models for Amino Acid Metabolism", European Journal of Pediatrics, vol. 156, 1997, pp. S2-S8.
Bier, D. M., "The Use of Stable Isotopes in Metabolic Investigation", Balliere's Clinical Endocrinology and Metabolism, vol. 1, No. 4, Nov. 1987, pp. 817-836.
Bingham, Sheila A., "The Use of 24-h Urine Samples and Energy Expenditure to Validate Dietary Assessments", The American Journal of Clinical Nutrition, vol. 59 (suppl), 1994, pp. 227S-231S.
Black et al., "Labeling DNA with Stable Isotopes: Economical and Practical Considerations", BioTechniques, vol. 30, 2001, pp. 134-138, 140.
Blair et al., "Changes in Physical Fitness and All-Cause Mortality. A Prospective Study of Healthy and Unhealthy Men", JAMA, vol. 273, 1995, pp. 1093-1098.

(56) References Cited

OTHER PUBLICATIONS

Blau et al., "Handbook of Derivatives for Chromatography", 2nd Edition, John Wiley & Sons Ltd., England, 1993, 8 pages.

Bonotto et al., "Study of the Distribution and Biological Effects of 3H in the Algae Acetabularia, Chlamydomonas and Porphyra", Current Topics in Radiation Research Quarterly, vol. 12, 1978, pp. 115-132.

Boros et al., "Genistein Inhibits Nonoxidative Ribose Synthesis in MIA Pancreatic Adenocarcinoma Cells: A New Mechanism of Controlling Tumor Growth", Pancreas, vol. 22, No. 1, 2001, pp. 1-7.

Boros et al., "Metabolic Profiling of Cell Growth and Death in Cancer: Applications in Drug Discovery", Drug Discovery Today, vol. 7, No. 6, Mar. 2002, pp. 364-372.

Bougnoux et al., "Fatty Acids and Breast Cancer: Sensitization to Treatments and Prevention of Metastatic Re-Growth", Frog Lipid Research, vol. 49, 2010, pp. 76-86.

Bowen et al., "Dealing with the Unknown: Metabolomics and Metabolite Atlases", Journal of American Society of Mass Spectrometry, 2010, pp. 1471-1476.

Bravo et al., "Decreased Hepatic Uptake and Processing of High Density Lipoprotein Unesterified Cholesterol and Cholesteryl Ester with Age in the Rat", Journal of Biochemistry, vol. 116, 1994, pp. 1088-1095.

Brown et al., "Treating Patients with Documented Atherosclerosis to National Cholesterol Education Program-Recommended Low-Density-Lipoprotein Cholesterol Goals with Atorvastatin, Fluvastatin, Lovastatin and Simvastatin", Journal of the American College of Cardiology, vol. 32, No. 3, 1998, pp. 665-672.

Buchanan, T. A., "Pancreatic Beta-Cell Loss and Preservation in Type 2 Diabetes", Clinical Therapeutics, vol. 25, Supplemental 2, Sep. 2003, pp. B32-B46.

Bucy et al., "Analysis of Lymph Node Biopsies in HIV Infected Patients before and After HAART", Abstract, 5th Conference on Retroviruses and Opportunistic Infections, Session 66, vol. 519, 1998, 177 Pages (Abstract only).

Busch et al., "Measurement of protein turnover rates by heavy water labeling of nonessential amino acids", Biochimica et Biophysica Acta, vol. 1760, 2006, pp. 730-744.

Caldwell et al., "Quantification of Peptide Isotopomer Abundances and Determination of Protein (sic) Turnover Rates by Using Mass Isotopomer Distribution Analysis", Abstract, 41st Annual Amer. Society Mass Spectrometry on Mass Spectrometry, 1993, p. 331a (Abstract only).

Carling et al., "Simultaneous Determination of Guanidinoacetate, Creatine and Creatinine in Urine and Plasma by Un-Derivatized Liquid Chromatography-Tandem Mass Spectrometry", Annals of Clinical Biochemistry, vol. 45, 2008, pp. 575-584.

Cassella et al., "Mechanisms of Lymphocyte Killing by HIV", Current Opinion in Hematology, vol. 4, 1997, pp. 24-31.

Cesar et al., "Direct Measurement of CD4+ and CD8+ T Cell Proliferation Rates in Vivo in AIDS Patients Using a Stable Isotope-Mass Spectrometric Technique", Abstract, 5th Conference on Retroviruses and Opportunistic Infections, Chicago Illinois., 1998, 1 page (Abstract only).

Chen et al., "Application of Probe Electrospray to Direct Ambient Analysis of Biological Samples", Rapid Commun Mass Spectrom, vol. 22, No. 15, Aug. 2008, pp. 2366-2374.

Chinkes et al., "Comparison of Mass Isotopomer Dilution Methods Used to Compute VLDL Production In Vivo", The American Journal of Physiology, vol. 271, 1996, pp. E373-E383.

Chobanian et al., "Body Cholesterol Metabolism in Man. II. Measurement of the Body Cholesterol Miscible Pool and Turnover Rate", Journal of Clinical Investigation, vol. 41, No. 9, 1962, pp. 1738-1744.

Christiansen et al., "Effect of Dietary Energy Restriction on Glucose Production and Substrate Utilization in Type 2 Diabetes", Diabetes, vol. 49, Oct. 2000, pp. 1691-1699.

Cichon et al., "Microenvironmental Influences that Drive Progression from Benign Breast Disease to Invasive Breast Cancer", J Mammary Gland Biol Neoplasia, vol. 15, Dec. 2010, pp. 389-397.

Clarke, R. B., "Isolation and Characterization of Human Mammary Stem Cells", Cell Proliferation, vol. 38, 2005, pp. 375-386.

Clayton, David A., "Replication and Transcription of Vertebrate Mitochondrial DNA", Annual Review of Cell Biology, vol. 7, 1991, pp. 453-478.

Cohen et al., "Purine and Pyrimidine Metabolism in Human T Lymphocytes. Regulation of Deoxyribonucleotide Metabolism", The Journal of Biological Chemistry, vol. 258, No. 20, 1983, pp. 12334-12340.

Cohen, J., "Failure Isn't What It Used to Be . . . But Neither is Success", Science, vol. 279, 1998, pp. 1133-1134.

Collins et al., "Measurement of Mitochondrial DNA Synthesis In Vivo Using a Stable Isotope-Mass Spectrometric Technique", Journal of Applied Physiology, vol. 94, 2003, pp. 2203-2211.

Collins et al., "A Method for Measuring Mitochondrial Proliferation In Vivo Using 2H20 Incorporation Into Mitochondria DNA", FASEB Journal, vol. 14, No. 4, Mar. 15, 2000, p. A620.

Commerford et al., "The Distribution of Tritium Among the Amino Acids of Proteins Obtained from Mice Exposed to Tritiated Water", Radiation Research, vol. 94, No. 1, 1983, pp. 151-155.

Comte et al., "Probing the Origin of Acetyl-CoA and Oxaloacetate Entering the Citric Acid Cycle from the 13C Labeling of Citrate Released by Perfused Rat Hearts", The Journal of Biological Chemistry, vol. 272, No. 42, Oct. 17, 1997, pp. 26117-26124.

Connors et al., "HIV Infection Induces Changes in CD4+ T-Cell Phenotype and Depletions Within the CD4+ T-Cell Repertoire that are Not Immediately Restored by Antiviral or Immune-Based Therapies", Nature Medicine, vol. 3, 1997, 533-540.

Conrads et al., "Stable Isotope Labeling in Proteomics", The Synthesis Cambridge Isotope Laboratories, vol. 3, No. 2, Jan. 2002, pp. 1-3.

Cornett et al., "MALDIImaging Mass Spectrometry: Molecular Snapshots of Biochemical Systems", Nature Methods, vol. 4, No. 10, 2007, pp. 828-833.

Craig et al., "The Impact of Physical Activity on Lipids, Lipoproteins, and Blood Pressure in Preadolescent Girls", Pediatrics, vol. 98, 1996, pp. 389-395.

Crain, Pamela F., "Preparation and Enzymatic Hydrolysis of DNA and RNA for Mass Spectrometry", Methods in Enzymology, vol. 193, 1990, pp. 782-790.

Dalvie, D., "Recent Advances in the Applications of Radioisotopes in Drug Metabolism, Toxicology and Pharmacokinetics", Current Pharmaceutical Design, vol. 6, 2000, pp. 1009-1028.

Davis et al., "Effect of Pinitol Treatment on Insulin Action in Subjects with Insulin Resistance", Diabetes Care, vol. 23, No. 7, Jul. 2000, pp. 1000-1005.

Deberardinis et al., "Brick by Brick: Metabolism and Tumor Cell Growth", Current Opinion in Genetics & Development, vol. 18, No. 1, Feb. 2008, pp. 54-61.

Deberardinis et al., "The Biology of Cancer: Metabolic Reprogramming Fuels Cell Growth and Proliferation", Cell Metabolism, Elsevier Incorporation, Jan. 2008, pp. 11-20.

Deeb et al., "Identification of an Integrated SV40 Tit-antigen Cancer Signature in Gressive Human Breast, Prostate, and Lung Carcinomas with Poor Prognosis", Cancer Research, vol. 67 No. 17, 2007, pp. 8065-8080.

Deeks et al., "CD4+ T Cell Kinetics and Activation in Human Immunodeficiency Virus-Infected Patients who Remain Viremic Despite Long-Term Treatment with Protease Inhibitor-Based Therapy", The Journal of Infectious Diseases, vol. 185, Feb. 1, 2002, pp. 315-323.

Deeks et al., "Viral Load and CD4+ T Cell Changes in Patients Failing Potent Protease Inhibitor Therapy", Abstract, 5th Conference on Retroviruses and Opportunistic Infections, Session 53, vol. 419, 1998, p. 158 (Abstract only).

Dekker et al., "Glucose Homeostasis in Children with Falciparum Malaria: Precursor Supply Limits Gluconeogenesis and Glucose Production", J Clin Endocrinol Metab., vol. 82, 1997, pp. 2514-2521.

Di Buono et al., "Comparison of Deuterium Incorporation and Mass Isotopomer Distribution Analysis for Measurement of Human Cholesterol Biosynthesis", Journal of Lipid Research, vol. 41, 2000, pp. 1516-1523.

(56) References Cited

OTHER PUBLICATIONS

Dimitrov et al., "Scientific Correspondence", Nature, vol. 375, 1995, pp. 194-195.
Diraison et al., "In Vivo Measurement of Plasma Cholesterol and Fatty Acid Synthesis with Deuterated Water: Determination of the Average Number of Deuterium Atoms Incorporated Metabolism", Metabolism: Clinical and Experimental, vol. 45, No. 7, Jul. 1996, pp. 817-821.
Dowsett et al., "Assessment of Ki67 in Breast Cancer: Recommendations From the International Ki67 in Breast Cancer Working Group", Journal of the National Cancer Institute, vol. 103, 2011, pp. 1656-1664.
Duane, Wiuiam C., "Measurement of Bile Acid Synthesis by three different Methods in Hypertriglyceridemic and Control Subjects", Journal of Lipid Research vol. 38, 1997, pp. 183-188.
Edes et al., "Glycemic Index and Insulin Response to a Liquid Nutritional Formula.Compared with a Standard Meal", Journal of the American College of Nutrition, vol. 17, No. 1, Jan. 1998, pp. 30-35.
Emken et al., "Incorporation of deuterium-labeled trans- and cis-13-octadeconoic acids in human plasma lipids", Journal of Lipid Research, vol. 24, 1983, pp. 34-41.
Emken, E. A., "Metabolism of Dietary Stearic Acid Relative to Other Fatty Acids in Human Subjects", The American Journal of Clinical Nutrition, vol. 60, (Suppl), 1994, pp. 1023S-1028S.
Eriksson et al., "Stimulation of Fecal Steroid Excretion After Infusion of Recombinant Proapolipoprotein A-1: Potential Reverse Cholesterol Transport in Humans", Circulation, vol. 100, 1999, pp. 594-598.
Etnier et al., "Metabolism of Organically Bound Tritium in Man", Radiation Research, vol. 100, 1984, pp. 487-502.
Evans et al., "Cachexia: A New Definition", Clinical Nutrition, vol. 27, 2008, pp. 793-799.
Evans, William J., "What is Sarcopenia?", The Journals of Gerontology Series A, vol. 50A, 1995, pp. 5-8.
Extended European Search Report (includes Supplementary European Search Report and Search Opinion) received for European Patent Application No. 12830717.0, mailed on Jan. 30, 2015, 8 pages.
Extended European Search Report received for European Application No. 12855131.4, mailed on Mar. 18, 2015, 8 pages.
Extended European Search Report received for European Patent Application No. 06759050.5, mailed on Mar. 31, 2011, 7 pages.
Extended European Search Report received for European Patent Application No. 06784805.1, mailed on Mar. 21, 2011, 7 pages.
Fagerquist et al., "Elimination of the Concentration Dependence in Mass Isotopomer Abundance Mass Spectrometry of Methyl Palmitate Using Metastable Atom Bombardment", Journal of the American Society of Mass Spectrometry, vol. 12, 2001, pp. 754-761.
Fagerquist et al., "Molecular Ion Fragmentation and its Effects on Mass Isotopomer Abundances of Fatty Acid Methyl Esters Ionized by Electron Impact", Journal of the American Society of Mass Spectrometry, vol. 10, 1999, pp. 430-439.
Feldman et al., "Chlordiazepoxide-Fluoxetine Interactions on Food Intake in Free-Feeding Rats", Pharmacology Biochemistry & Behavior, vol. 8, No. 6, 1978, pp. 749-752.
Ferezou et al., "Origins of Neutral Sterols in Human Feces Studied by Stable Isotope Labeling Deuterium and Carbon-13 Existence of an External Secretion of Cholesterol", Digestion, vol. 21, No. 5, 1981, pp. 232-243.
Fiaccadori et al., "Skeletal Muscle Energetics, Acid-Base Equilibrium and Lactate Metabolism in Patients with Severe Hypercapnia and Hypoxemia", Chest, vol. 92, No. 5, Nov. 1987, pp. 883-887.
Final Office Action received for U.S. Appl. No. 11/416,842 mailed on Jun. 16, 2015, 16 pages.
Futami et al., "An Application of the On-line Respiratory Mass Spectrometer to the Detection of Helicobacter pylori Infection Using 13C-Labeled Urea", Journal of the Mass Spectrometry Society of Japan, vol. 47, No. 6, 1999, pp. 386-388.

Gasparini et al., "Amplification of DNA from Epithelial Cells in Urine", The New England Journal of Medicine, vol. 320, No. 12, 1989, p. 809.
Gerling et al., "Prediction of Liver Fibrosis According to Serum Collagen VI Level in Children with Cystic Fibrosis", The New England Journal of Medicine, vol. 336, No. 22, 1997, pp. 1611-1612.
Gerlinger et al., "Intratumor Heterogeneity and Branched Evolution Revealed by Multiregion Sequencing", The New England journal of medicine, vol. 366, No. 10, Mar. 8, 2012, pp. 883-892.
Gorochov et al., "Perturbation of CD4+ and CD8+ T-Cell Repertoires During Progression to AIDS and Regulation of the CD4+ Repertoire During Antiviral Therapy", Nature Medicine, vol. 4, 1998, pp. 215-221.
Goz, Barry, "The Effects of Incorporation of 5-Halogenated Deoxyuridines into the DNA of Eukaryotic Cells", Pharmacological Reviews, vol. 29, 1977, pp. 249-272.
Gratzner, "Monoclonal Antibody to 5-Bromo- and 5-Iododeoxyuridine: A New Reagent for Detection of DNA Replication", Science, vol. 218, 1982, pp. 474-475.
Green et al., "The C3(1)/SV40 T-Antigen Transgenic Mouse Model of Mammary Cancer: Ductal Epithelial Cell Targeting with Multistage Progression to Carcinoma", Oncogene, vol. 19, 2000, pp. 1020-1027.
Greving et al., "Nanostructure-Initiator Mass Spectrometry Metabolite Analysis and Imaging", Analytical Chemistry, vol. 83, No. 1, Jan. 1, 2011, pp. 2-7.
Guillermet-Guibert et al., "Targeting the Sphingolipid Metabolism to Defeat Pancreatic Cancer Cell Resistance to the Chemotherapeutic Gemcitabine Drug", Molecular Cancer Therapeutics, vol. 8, No. 4, Apr. 2009, pp. 809-821.
Guo et al., "De Novo Lipogenesis in Adipose Tissue of Lean and Obese Women: Application of Deuterated Water and Isotope Ratio Mass Spectrometry", International Journal of Obesity and Related Metabolic Disorders, vol. 24, 2000, pp. 932-937.
Gygi et al., "Using Mass Spectrometry for Quantitative Proteomics", Proteomics: A Trends Guide, 2000, pp. 31-36.
Hanahan et al., "Hallmarks of Cancer: The Next Generation", Cell, vol. 144, No. 5, 2011, pp. 646-674.
Hankin et al., "Relationship between MALDI IMS Intensity and Measured Quantity of Selected Phospholipids in Rat Brain Sections", Anal Chemistory, vol. 82, No. 20, 2010, pp. 8476-8484.
Hansen et al., "A Practical Method for Uniform Isotopic Labeling of Recombinant Proteins in Mammalian Cells", Biochemistry, vol. 31, 1992, pp. 12713-12718.
Harris et al., "Elevation of Creatine in Resting and Exercised Muscle of Normal Subjects by Creatine Supplementation", Clinical Science, vol. 83, 1992, pp. 367-374.
Heck et al., "Posttranslational Amino Acid Epimerization: Enzyme-Catalyzed Isomerization of Amino Acid Residues in Peptide Chains", Proceedings of the National Academy of Sciences of the United States of America, vol. 93, Apr. 1996, pp. 4036-4039.
Hellerstein et al., "Mass Isotopomer Distribution Analysis: A Technique for Measuring Biosynthesis and Turnover of Polymers", The American Journal of Physiology, vol. 263, 1992, pp. E988-E1001.
Hellerstein et al., "Altered Fluxes Responsible for Reduced Hepatic Glucose Production and Gluconeogenesis by Exogenous Glucose in Rats", The American Journal of Physiology, vol. 272, 1997, pp. E163-E172.
Hellerstein et al., "Directly Measured Kinetics of Circulating T Lymphocytes in Normal and HIV-1-Infected Humans", Nature Medicine, vol. 5, 1999, pp. 83-89.
Hellerstein et al., "Effects of Cigarette Smoking and its Cessation on Lipid Metabolism and Energy Expenditure in Heavy Smokers", J. Clin. Invest., vol. 93, 1994, pp. 265-272.
Hellerstein et al., "Glycoconjugates as Noninvasive Probes of Intrahepatic Metabolism: Pathways of Glucose Entry into Compartmentalized Hepatic UDP-glucose Pools during Glycogen Accumulation", Proceedings of the National Academy of Sciences of the United States of America, vol. 83, No. 18, 1986, pp. 7044-7048.

(56) References Cited

OTHER PUBLICATIONS

Hellerstein et al., "Hepatic Gluconeogenic Fluxes and Glycogen Turnover During Fasting in Humans. A Stable Isotope Study", The Journal of Clinical Investigation, vol. 100, No. 5, Sep. 1997, pp. 1305-1319.
Hellerstein et al., "Mass Isotopomer Distribution Analysis at Eight Years: Theoretical, Analytic, and Experimental Considerations", The American Journal of Physiology, vol. 276, 1999, pp. E1146-E1170.
Hellerstein et al., "Mass Isotopomer Distribution Analysis for Measuring Fluxes Through Intracellular Metabolic Pathways and Biosynthetic Rates of Polymers", IFAC Modeling and Control in Biomedical Systems, 1994, pp. 353-359.
Hellerstein et al., "Measurement of De Novo Hepatic Lipogenesis in Humans Using Stable Isotopes", Journal of Clinical Investigation, vol. 87, May 1991, pp. 1841-1852.
Hellerstein et al., "Measurement of Hepatic Ra UDP-glucose in Vivo in Rats: Relation to Glycogen Deposition and Labeling Patterns", The American Journal of Physiology, vol. 272, 1997, pp. E155-E162.
Hellerstein et al., "Measurement of Synthesis Rates of Slow-turnover Proteins from 2H2O Incorporation into Non-essential Amino Acids (NEAA) and Application of Mass Isotopomer Distribution Analysis (MIDA)", Faseb Journal Experimental Biology 2002: Meeting, vol. 16, 2002, p. A256 (Abstract only).
Hellerstein et al., "Model for Measuring Absolute Rates of Hepatic de Novo Lipogenesis and Reesterification of Free Fatty Acids", The American Journal of Physiology, vol. 265, 1993, pp. E814-E820.
Hellerstein et al., "Subpopulations of Long-Lived and Short-Lived T Cells in Advanced HIV-1 Infection", The journal of Clinical Investigation, vol. 112, No. 6, 2003, pp. 956-966.
Hellerstein et al., "T Cell Turnover in HIV-1 Disease", Immunity, vol. 7, 1997, pp. 583-589.
Hellerstein, M. K., "New Stable Isotope-Mass Spectrometric Techniques for Measuring Fluxes through Intact Metabolic Pathways in Mammalian Systems: Introduction of Moving Pictures into Functional Genomics and Biochemical Phenotyping", Metabolic Engineering, vol. 6, 2004, pp. 85-100.
Hellerstein, M. K., "Carbohydrate-Induced Hypertriglyceridemia: Modifying Factors and Implications for Cardiovascular Risk", Curr. Opin. Lipidology, vol. 13, 2002, pp. 33-40.
Hellerstein, M. K., "Measurement of T-Cell Kinetics: Recent Methodologic Advances", Trends Immunology Today, vol. 20, No. 10, 1999, pp. 438-441.
Hellerstein, M. K., "Methods for Measurement of Fatty Acid and Cholesterol Metabolism", Current Opinion in Lipidology, vol. 6, 1995, pp. 172-181.
Hellerstein, M. K., "No Common Energy: de Novo Lipogenesis as the Road Less Traveled", The American Journal of Clinical Nutrition, vol. 74, 2001, pp. 707-708.
Hellerstein, M. K., "Synthesis of Fat in Response to Alterations in Diet: Insights from New Stable Isotope Methodologies", Lipids 31(Supp), 1996, pp. S117-S125.
Hellerstein, M. K., "The Changing Face of AIDS: Translators Needed", The American Journal of Clinical Nutrition, vol. 70, 1999, pp. 787-788.
Hellerstein, Marc K., "In Vivo Measurement of Fluxes Through Metabolic Pathways: The Missing Link in Functional Genomics and Pharaceutical Research", Annu. Rev. Nutr., vol. 23, 2003, pp. 379-402.
Herschkowitz et al., "The Functional Loss of the Retinoblastoma Tumour Suppressor is a Common Event in Basal-Like and Luminal B Breast Carcinomas", Breast Cancer Research, vol. 10, No. 5, Sep. 2008, 13 pages.
Heymsfield et al., "Perspective in Nutirition Measurement of Muscle Mass in Humans: Validity of the 24-hour Urinary Creatinine Method", American Journal of Clinical Nutrition, vol. 37, Mar. 1983, pp. 478-494.
Hilvo et al., "Novel Theranostic Opportunities Offered by Characterization of Altered Membrane Lipid Metabolism in Breast Cancer Progression", Cancer Research, vol. 71, 2011, pp. 3236-3245.
Hinkson et al., "The Dynamic State of Protein Turnover: It's About Time", Trends in Cell Biology, vol. 21, No. 5, May 2011, pp. 293-303.
Ho et al., "Rapid Turnover of Plasma Virions and CD4 Lymphocytes in HIV-1 Infection", Nature, vol. 373, 1995, pp. 123-126.
Hoh et al., "De Novo Lipogenesis Predicts Short-Term Body-Composition Response by Bioelectrical Impedance Analysis to Oral Nutritional Supplements in HIV-Associated Wasting", The American Journal of Physiology, vol. 68, 1998, pp. 154-163.
Hsieh et al., "Dynamics of Keratinocytes in Vivo Using 2H2O Labeling: A Sensitive Marker of Epidermal Proliferation State", J. Invest. Dermatol, vol. 123, 2004, pp. 530-536.
Hsu et al., "Cancer Cell Metabolism: Warburg and Beyond", Cell, vol. 134, Sep. 5, 2008, pp. 703-707.
Hudgins et al., "Human Fatty Acid Synthesis is Stimulated by a Eucaloric Low Fat, High Carbohydrate Diet", J. Clin. Invest., vol. 97, No. 9, 1996, pp. 2081-2091.
Hudgins et al., "Relationship Between Carbohydrate-Induced Hypertriglyceridemia and Fatty Synthesis in Lean and Obese Subjects", J. Lipid Res., vol. 41, 2000, pp. 595-604.
Hughes et al., "Developments in Quantitative Mass Spectrometry for the Analysis of Proteome Dynamics", Trends in Biotechnology, vol. 30, No. 12, Dec. 2012, pp. 668-676.
Hulzebos et al., "Measurement of Parameters of Cholic Acid Kinetics in Plasma using a Microscale Stable Isotope Dilution Technique: Application to Rodents and Humans", Journal of Lipid Research, vol. 42, 2001, pp. 1923-1929.
Humphrey et al., "A New Method for the Measurement of Protein Turnover", Biochem. J., vol. 148, 1975, pp. 119-127.
Humphrey et al., "A Sensitive Method for Measuring Protein Turnover Based on the Measurement of 2-3H-labeled Amino Acids in Proteins", Biochem. J., vol. 156, 1976, pp. 561-568.
Igal, R. Ariel, "Stearoyl-CoA desaturase-1: A Novel Key Player in the Mechanisms of Cell Proliferation, Programmed Cell Death and Transformation to Cancer", Carcinogenesis, vol. 31, No. 9, 2010, pp. 1509-1515.
International Preliminary Report on Patentability received for PCT Patent Application No. PCT/US2004/021063 issued on Jan. 3, 2006, 4 pages.
International Preliminary Report on Patentability received for PCT Patent Application No. PCT/US2004/039722, issued on May 29, 2006, 4 pages.
International Preliminary Report on Patentability received for PCT Patent Application No. PCT/US2005/005660, issued on Oct. 30, 2007, 5 pages.
International Preliminary Report on Patentability received for PCT Patent Application No. PCT/US2012/054329, mailed on Mar. 20, 2014, 11 pages.
International Preliminary Report on Patentability received for PCT Patent Application No. PCT/US2012/068068, mailed on Jun. 19, 2014, 7 pages.
International Preliminary Report on Patentability received for PCT Patent Application No. PCT/US2014/028931, mailed on Sep. 24, 2015, 6 pages.
International Preliminary Report on Patentability received for PCT Patent Application No. PCT/US2014/042186, mailed on Dec. 23, 2015, 8 pages.
International Search Report & Written Opinion received for PCT Patent Application No. PCT/US2014/042186, mailed on Oct. 1, 2014, 10 pages.
International Search Report and Written Opinion received for PCT Patent Application No. PCT/US2005/005660, mailed on Oct. 11, 2007, 6 pages.
International Search Report and Written Opinion received for PCT Patent Application No. PCT/US2005/010429, mailed on Aug. 8, 2006, 15 pages.
International Search Report and Written Opinion received for PCT Patent Application No. PCT/US2006/017167, mailed on Feb. 5, 2008, 11 pages.

(56) References Cited

OTHER PUBLICATIONS

International Search Report and Written Opinion received for PCT Patent Application No. PCT/US2012/054329, mailed on Dec. 7, 2012, 13 pages.
International Search Report and Written Opinion received for PCT Patent Application No. PCT/US2014/028931, mailed on Jul. 21, 2014, 9 pages.
International Search Report received for PCT Patent Application No. PCT/US1998/009479, mailed on Oct. 20, 1998, 3 pages.
International Search Report received for PCT Patent Application No. PCT/US2002/033996, mailed on Jun. 19, 2003, 2 pages.
International Search Report received for PCT Patent Application No. PCT/US2003/004183, mailed on Jun. 29, 2004, 3 pages.
International Search Report received for PCT Patent Application No. PCT/US2003/010554, mailed on Aug. 20, 2004, 4 pages.
International Search Report received for PCT Patent Application No. PCT/US2003/020052, mailed on Apr. 13, 2004, 3 pages.
International Search Report received for PCT Patent Application No. PCT/US2003/023340, mailed on Aug. 18, 2004, 3 pages.
International Search Report received for PCT Patent Application No. PCT/US2003/027623, mailed on Jul. 8, 2004, 4 pages.
International Search Report received for PCT Patent Application No. PCT/US2003/029361, mailed on Jan. 19, 2005, 4 pages.
International Search Report received for PCT Patent Application No. PCT/US2003/035107, mailed on Jul. 9, 2004, 1 page.
International Search Report received for PCT Patent Application No. PCT/US2003/29526, mailed on Aug. 18, 2004, 1 page.
International Search Report received for PCT Patent Application No. PCT/US2004/039722, mailed on Mar. 25, 2005, 3 pages.
International Search Report received for PCT Patent Application No. PCT/US2004/21063, mailed on Apr. 4, 2005, 1 page.
International Search Report received for PCT Patent Application No. PCT/US2005/08265, mailed on Aug. 1, 2005, 4 pages.
International Search Report received for PCT Patent Application No. PCT/US2012/068068, mailed on Feb. 8, 2013, 3 pages.
International Written Opinion received for PCT Patent Application No. PCT/US2004/039722, mailed on Mar. 25, 2005, 3 pages.
International Written Opinion received for PCT Patent Application No. PCT/US2012/068068, mailed on Feb. 8, 2013, 5 pages.
Iyengar et al., "Human Stools as a Source of Viable Colonic Epithelial Cells", The FASEB Journal, vol. 5, 1991, pp. 2856-2859.
James, J. S., "Clinical Implications of Virological Failure: Interview with Steven Deeks, M.D., San Francisco General Hospital", AIDS Treatment News, vol. 289, 1998, pp. 6-7.
Janssen et al., "Linking Age-Related Changes in Skeletal Muscle Mass and Composition with Metabolism and Disease", The Journal of Nutrition, Health & Aging, vol. 9, No. 6, 2005, pp. 408-419.
Janssen et al., "The Healthcare Costs of Sarcopenia in the United States", Journal of the American Geriatrics Society, vol. 52, No. 1, Jan. 2004, pp. 80-85.
Jennings et al., "The Use of Infrared Spectrophotometry for Measuring Body Water Spaces", Clinical Chemistry, vol. 45, No. 7, Jul. 1999, pp. 1077-1081.
Jiang et al., "Rb Deletion in Mouse Mammary Progenitors Induces Luminal-B or Basal-Like/EMT Tumor Subtypes Depending on P53 Status", The Journal of Clinical Investigation, vol. 120, No. 9, Sep. 2010, pp. 3296-3309.
Jones et al., "An Integrated 2H and 13C NMR Study of Gluconeogenesis and TCA Cycle Flux in Humans", American Journal of Physiology-Endocrinology and Metabolism, vol. 281, 2001, pp. E848-856.
Jones et al., "Evidence for Diurnal Periodicity in Human Cholesterol Synthesis", Journal of Lipid Research, vol. 31, 1990, pp. 667-673.
Jones et al., "Interaction of Dietary Fat Saturation and Cholesterol Level on Cholesterol Synthesis Measured Using Deuterium Incorporation", Journal of Lipid Research, vol. 35, 1994, pp. 1093-1101.
Jones et al., "Modulation of Plasma Lipid Levels and Cholesterol Kinetics by Phytosterol Versus Phytostanol Esters", Journal of Lipid Research, vol. 41, 2000, pp. 697-705.
Jones et al., "Multiple Statistical Analysis Techniques Corroborate Intratumor Heterogeneity in Imaging Mass Spectrometry Datasets of Myxofibrosarcoma", PLOS One, vol. 6, No. 9, Sep. 29, 2011, 11 pages.
Jung et al., "Metabolic Adaptations to Dietary Fat Malabsorption in Chylomicron-Deficient Mice", Biochem. J., vol. 343, 1999, pp. 473-478.
Jungas, Robert L., "Fatty Acid Synthesis in Adipose Tissue Incubated in Tritiated Water", Biochemistry, vol. 7, No. 10, 1968, pp. 3708-3717.
Jurchen et al., "MALDI-MS Imaging of Features Smaller than the Size of the Laser Beam", Journal of American Society for Mass Spectrometry, Published by Elsevier Incorporation, vol. 16, Aug. 10, 2005, pp. 1654-1659.
Kasumov et al., "Measuring Protein Synthesis using Metabolic 2H Labeling, High-Resolution Mass Spectrometry, and an Algorithm", Analytical Biochemistry, vol. 412, 2011, pp. 47-55.
Katz et al., "Futile Cycles in the Metabolism of Glucose", Curr Top Cell Regul, vol. 10, 1976, pp. 237-289.
Kelleher et al., "Model Equations for Condensation Biosynthesis Using Stable Isotopes and Radioisotopes", Am. J. Physiol., vol. 262, 1992, pp. E118-E125.
Kennecke et al., "Metastatic Behavior of Breast Cancer Subtypes", Journal of Clinical Oncology, vol. 28, No. 20, Jul. 2010, pp. 3271-3277.
Khairallah et al., "Assessment of Protein Turnover in Perfused Rat Liver: Evidence for Amino Acid Compartmentation from Differential Labeling of Free and tRNA-bound Valine", J Biol Chem, vol. 251, No. 5, 1976, pp. 1375-1384.
Kim et al., "A New Stable Isotope-Mass Spectrometric (MS) Method to Measure Proliferation Rates of Colon Epithelial Cells", Faseb. Journal, vol. 14, No. 4, 2000, p. A718.
Kito et al., "Mass Spectrometry-Based Approaches toward Absolute Quantitative Proteomics", Current Genomics, vol. 9, No. 4, Jun. 2008, pp. 263-274.
Koeniger et al., "A Quantitation Method for Mass Spectrometry Imaging", Rapid Communications in Mass Spectrometry, vol. 25, No. 4, 2011, pp. 503-510.
Kreisberg et al., "Measurement of Muscle Mass in Humans by Isotopic Dilution of Creatine-14C", Journal of Applied Physiology, vol. 28, No. 3, Mar. 1970, pp. 264-267.
Lammert et al., "Effects of Isoenergetic Overfeeding of Either Carbohydrate or Fat in Young Men", British Journal of Nutrition, vol. 84, 2000, pp. 233-245.
Landau et al., "Use of 2H2O for Estimating Rates of Gluconeogenesis", Journal of Clinical Investigation, vol. 95, Jan. 1995, pp. 172-178.
Lechene et al., "High-Resolution Quantitative Imaging of Mammalian and Bacterial Cells using Stable Isotope Mass Spectrometry", Journal of Biology, vol. 5, Article 20, Oct. 2006, pp. 20.1-20.30.
Lee et al., "Cardiorespiratory Fitness, Body Composition, and All-Cause and Cardiovascular Disease Mortality in Men 1-3", Am. J. Clin. Nutr., vol. 69, 1999, pp. 373-380.
Lee et al., "In Vivo Measurement of Fatty Acids and Cholesterol Synthesis using D20 and Mass Isotopomer Analysis", American Journal of Physiology—Endocrinology and Metabolism, vol. 266, No. 5, 1994, pp. E699-E708.
Lee et al., "Mass Spectrometry-Based metabolomics, Analysis of Metabolite-protein Interactions, and Imaging", NIH Public Access Biotechniques, vol. 49, No. 2, Aug. 2010, pp. 557-565.
Lee et al., "Resolving Brain Regions Using Nanostructure Initiator Mass Spectrometry Imaging", Integrative Biology, vol. 4, No. 6, Jun. 2012, pp. 693-699.
Lefebvre, Pierre J., "Naturally Labeled 13C-Glucose: A New Tool to Measure Oxidation Rates of Exogenous Glucose", Diabetes 28(Suppl. 1), Jan. 1979, pp. 63-65.
Leung et al., "A Deficiency of Microsomal Triglyceride Transfer Protein Reduces Apolipoprotein B Secretion", The Journal of Biological Chemistry, vol. 275, No. 11, 2000, pp. 7515-7520.
Lewanczuk et al., "Comparison of the [13 C] Glucose Breath Test to the Hyperinsulinemic-Euglycemic Clamp When Determining Insulin Resistance", Diabetes Care, vol. 27, No. 2, 2004, pp. 441-447.

(56) References Cited

OTHER PUBLICATIONS

Liedtke et al., "Response to Neoadjuvant Therapy and Long-Term Survival in Patients with Triple-Negative Breast Cancer", Journal of Clinical Oncology, vol. 26, No. 8, Mar. 2008, pp. 1275-1281.
Lindwal et al., "Heavy Water Labeling of Keratin as a Non-Invasive Biomarker of Skin Turnover In Vivo in Rodents and Humans", Journal of Investigative Dermatology, vol. 126, 2006, pp. 841-848.
Linn et al., "Effect of Long-Term Dietary Protein Intake on Glucose Metabolism in Humans", Diabetologia, vol. 43, 2000, pp. 1257-1265.
Lipkin et al., "Cell Proliferation Kinetics in the Gastrointestinal Tract of Man. I. Cell Renewal in Colon and Rectum", Journal of Clinical Investigations, vol. 42, No. 6, 1963, pp. 767-776.
Lipkin, Martin, "Proliferation and Differentiation of Normal and Diseased Gastrointestinal Cells", In Physiology of the Gastrointestinal Tract, L.R. Johnson ed., Raven Press, New York, 1987, pp. 255-284.
Liu et al., "Polarity and Proliferation are Controlled by Distinct Signaling Pathways Downstream of PI3-kinase in Breast Epithelial Tumor Cells", The Journal of Cell Biology, vol. 164, No. 4, Feb. 16, 2004, pp. 603-612.
Lu et al., "SILAM for Quantitative Proteomics of Liver Akt1/PKBα after Burn Injury", International Journal of Molecular Medicine, vol. 29, No. 3, Mar. 2012, pp. 461-471.
Lukaski, Henry C., "Methods for the Assessment of Human body Composition: Traditional and New", The American Journal of Clinical Nutrition, vol. 46, No. 4, Jan. 1, 1987, pp. 537-556.
Lutton et al., "Critical analysis of the Use of 14C-acetate for Measuring In Vivo Rat Cholesterol Synthesis", Reprod. Nutr. Dev., vol. 30, 1990, pp. 71-84.
MacAllan et al., "Measurement of Cell Proliferation by Labeling of DNA with Stable Isotope-Labeled Glucose: Studies in Vitro, in Animals, and in Humans", Proc. Natl. Acad. Sci., vol. 95, 1998, pp. 708-713.
Maentausta et al., "Radioimmunoassay of Conjugated Cholic Acid, Chenodeoxycholic Acid, and Deoxycholic Acid from Human Serum, with Use of 125I-Labeled Ligands", Clin. Chem., vol. 25, No. 2, 1979, pp. 264-268.
Maheo et al., "Differential Sensitization of Cancer Cells to Doxorubicin by DHA: A Role for Lipoperoxidation", Free Radical Biology and Medicine, vol. 39, 2005, pp. 742-751.
Malberg et al., "Chronic Antidepressant Treatment Increases Neurogenesis in Adult Rat Hippocampus", The Journal of Neuroscience, vol. 20, No. 24, Dec. 15, 2000, pp. 9104-9110.
Margolick et al., "Failure of T-cell Homeostasis Preceding AIDS in HIV-1 Infection", Nature Medicine, vol. 1, No. 7, 1995, pp. 674-680.
Maric et al., "Functional Ionotropic Glutamate Receptors Emerge During Terminal Cell Division and Early Neuronal Differentiation of Rat Neuroepithelial Cells", Journal of Neuroscience Research, vol. 61, No. 6, 2000, pp. 652-662.
Marin et al., "Dynamic Profiling of the Glucose Metabolic Network in Fasted Rat Hepatocytes using [1,2-13C2]Glucose", Biochemical Journal, vol. 381, 2004, pp. 287-294.
Martin et al., "Discovery of a Human Liver Glycogen Phosphorylase Inhibitor that Lowers Blood Glucose in Vivo", Proc. Natl. Acad. Sci. USA, vol. 95, No. 4, 1998, pp. 1776-1781.
Marusyk et al., "Tumor Heterogeneity: Causes and Consequences", Biochimical Biophysical Acta, vol. 1805, No. 1, Jan. 2010, pp. 105-117.
Mathur-De Vre et al., "Molecular Aspects of Tritiated Water and Natural Water in Radiation Biology", Prog. Biophys. Molec. Biol., vol. 43, 1984, pp. 161-193.
McCloskey, James A., "ElectronIonization Mass Spectra of Trimethylsilyl Derivatives of Nucleosides", Meth. Enz., vol. 193, 1990, pp. 825-841.
McCubrey et al., "Roles of the Raf/MEK/ERK Pathway in Cell Growth, Malignant Transformation and Drug Resistance", Biochimical Biophysical Acta, vol. 1773, 2007, pp. 1263-1284.

McCune et al., "Factors Influencing T-Cell Turnover in HIV-1-Seropositive Patients", Journal of Clinical Investigation, vol. 105, 2000, pp. R1-R8.
McCune, J. M., "Thymic Function in HIV-1 Disease", Seminars in Immunology, vol. 9, 1997, pp. 397-404.
McFarland et al., "Inhibition of DNA Synthesis in Neonatal Rat Brain Regions Caused by Acute Nicotine Administration", Developmental Brain Research, vol. 58, No. 2, Feb. 22, 1991, pp. 223-229.
McLean et al., "In Vivo Estimates of Division and Death Rates of Human T Lymphocytes", Proc. Natl. Acad. Sci. USA, vol. 92, 1995, pp. 3707-3711.
McMahon et al., "Quantitative Imaging of Cells with Multiisotope Imaging Mass Spectrometry (MIMS)—Nanoautography with Stable Isotope Tracers", National Resource for Imaging Mass Spectrometry, vol. 252, No. 19, Jul. 30, 2006, pp. 6895-6906.
Meier et al., "Rates of Protein Synthesis and Turnover in Fetal Life", Am. J. Physiol., vol. 240, No. 3, 1981, pp. E320-E324.
Mellors et al., "Prognosis in HIV-1 Infection Predicted by the Quantity of Virus in Plasma", Science, vol. 272, 1996, pp. 1167-1170.
Mellors et al., "Quantitation of HIV-1 RNA in Plasma Predicts Outcome after Seroconversion", Ann. Intern. Med., vol. 122, 1995, pp. 573-579.
Messmer et al., "In Vivo Measurements Document the Dynamic Cellular Kinetics of Chronic Lymphocytic Leukemia B Cells", The Journal of Clinical Investigation, vol. 115, No. 3, Mar. 2005, pp. 755-764.
Mewissen et al., "Comparative Incorporation of Tritium from Tritiated Water Versus Tritiated Thymidine, Uridine or Leucine", Curr Top. Rad. Res. Quart, vol. 12, 1977, pp. 225-254.
Michie et al., "Lifespan of Human Lymphocyte Subsets Defined by CD45 Isoforms," Nature, vol. 360, 1992, pp. 264-265.
Mikkola et al., "Serum Cholesterol Efflux Potential is an Independent Predictor of Coronary Artery Atherosclerosis", Atherosclerosis, vol. 170, 2003, pp. 31-38.
Mindham et al., "Application of Simultaneous Spleen and Liver Perfusion to the Study of Reverse Cholesterol Transport", Biochemical Journal, vol. 302, 1994, pp. 207-213.
Misell et al., "A new in Vivo Stable Isotope Method for Measuring Mammary Epithelial Cell Proliferation", Faseb Journal Experimental Biology 2000, vol. 14, No. 4, 2000, p. 550.
Mohri et al., "Increased Turnover of T Lymphocytes in HIV-1 Infection and its Reduction by Antiretroviral Therapy", J. Exp. Med., vol. 194, No. 9, 2001, pp. 1277-1287.
Morris et al., "Evidence that a Slowly Cycling Subpopulation of Adult Murine Epidermal Cells Retains Carcinogen", Cancer Research, vol. 46, 1997, pp. 3061-3066.
Morris et al., "Evidence that Cutaneous Carcinogen-initiated Epithelial Cells from Mice are Quiescent Rather than Actively Cycling", Cancer Research, vol. 57, 1997, pp. 3436-3443.
Morsches et al., "Tierexperimentelle Untersuchungen Uber Die Beziehungen Zwischen Der Hydroxyprolinausscheidung Im Urin Und Den Hydroxyprolinfraktionen Im Serum", Der Hautarzt, vol. 27, 1976, pp. 234-242.
Mosier, D. E., "CD4.sup.+ Cell Turnover", Nature, vol. 375, 1995, pp. 193-194.
Murali-Krishna et al., "Counting Antigen-Specific CD8 T Cells: A Reevaluation of Bystander Activation during Viral Infection", Immunity, vol. 8, 1998, pp. 177-187.
Murphy et al., "A New, Sensitive in Vivo Diagnostic Test of Insulin Resistance: The Deuterated Oral Glucose Tolerance Test (2H-OGTT)", Diabetes, American Diabetes Association, US, vol. 53, No. Suppl. 02, Jan. 1, 2004, 2 pages.
Murphy et al., "Imaging of Lipid Species by MALDI Mass Spectrometry", Journal of Lipid Research, Apr. 2009, pp. S317-S322.
Mussini et al., "Determination of Creatine in Body Fluids and Muscle", Journal of Chromatography, Biomedical Applications, vol. 305, 1984, pp. 450-455.
Nagasaka et al., "Endogenous Glucose Production and Glucose Effectiveness in Type 2 Diabetic Subjects Derived From Stable-Labeled Minimal Modal Approach", Diabetes, vol. 48, May 1999, pp. 1054-1056.

(56) References Cited

OTHER PUBLICATIONS

Naik et al., "Pharmacological Activation of Liver X Receptors Promotes Reverse Cholesterol Transport In Vivo", Circulation, vol. 113, 2006, pp. 90-97.
Nanjee et al., "Intravenous apoA-I/lecithin Discs Increase Pre-Beta-HDL Concentration in Tissue Fluid and Stimulate Reverse Cholesterol Transport in Humans", Journal of Lipid Research, vol. 42, 2001, pp. 1586-1593.
"NCBI Blast: Protein Sequence (17 letters)", Available at: <http://blast.ncbi.nlm.nih.gov/Blast.cgi>, Visited on May 29, 2008, 5 pages.
Neese et al., "Measurement in Vivo of Proliferation Rates of Slow Turnover Cells by 2H2O Labeling of the Deoxyribose Moiety of DNA", Proceedings of the National Academy of Sciences, vol. 99, No. 24, Nov. 26, 2002, pp. 15345-15350.
Neese et al., "Advances in the Stable Isotope-Mass Spectrometric Measurement of DNA Synthesis and Cell Proliferation", Analytical Biochemistry, vol. 298, No. 2, 2001, pp. 189-195.
Neese et al., "Gluconeogenesis and Intrahepatic Triose Phosphate Flux in Response to Fasting or Substrate Loads", Journal of Biological Chemistry, vol. 270, No. 24, 1995, pp. 14452-14463.
Neese et al., "Measurement of Endogenous Synthesis of Plasma Cholesterol in Rats and Humans Using MIDA", Am. J. Physiol., vol. 264, 1993, pp. E139-E147.
Neher et al., "Pyruvate and Thiamine Pyrophosphate Potentiate Cyclic Nucleotide-Induced Steroidogenesis in Isolated Rat Adrenocortical Cells", J.Steroid Biochem., vol. 18, 1983, pp. 1-6.
Neve et al., "A Collection of Breast Cancer Cell Lines for the Study of Functionally Distinct Cancer Subtypes", Cancer Cell, vol. 10, No. 6, Dec. 2006, pp. 515-527.
"New Diagnostic Technique Could Help Treat AIDS", Agence France-Presse, Dow Jones News, Feb. 17, 1998, pp. 1-2.
Non-Final Office Action received for U.S. Appl. No. 14/363,779, mailed on Jan. 25, 2016, 8 pages.
Nordhoff et al., "Mass Spectroscopy of Nucleic Acids", Mass Spectrometry Reviews, vol. 15, No. 2, 1998, pp. 67-138.
Nordström et al., "Metabolomics: Moving to the Clinic", Journal of Neuroimmune Pharmacology, vol. 5, No. 1, 2009, pp. 4-17.
Northen et al., "Clathrate Nanostructures for Mass Spectrometry", Nature, vol. 449, No. 7165, Oct. 25, 2007, pp. 1033-1036.
Northen et al., "Nanostructure-Initiator Mass Spectrometry-Based Enzyme Activity Assay", PNAS, vol. 105, No. 10, Mar. 11, 2008, pp. 3678-3683.
Notice of Allowance received for Canadian Patent Application No. 2,475,924, mailed on Sep. 17, 2015, 1 page.
Notice of Allowance received for U.S. Appl. No. 14/210,415, mailed on May 15, 2015, 6 pages.
Office Action Received for European Patent Application No. 12855131.4, mailed on Dec. 1, 2015, 4 pages.
Ogretmen et al., "Biologically Active Sphingolipids in Cancer Pathogenesis and Treatment", Nature Reviews Cancer, vol. 4, No. 8, 2004, pp. 604-616.
Ong et al., "Stable Isotope Labeling by Amino Acids in Cell Culture, SILAC, as a Simple and Accurate Approach to Expression Proteomics", Molecular and Cellular Proteomics, vol. 1.5, 2002, pp. 376-386.
Oshima et al., "COX Selectivity and Animal Models for Colon Cancer", Current Pharmaceutical Design, vol. 8, 2002, pp. 1021-1034.
Ouguerram et al., "A New Labeling Approach Using Stable Isotopes to Study In Vivo Plasma Cholesterol Metabolism in Humans", Metabolism, vol. 51, No. 1, Jan. 2002, pp. 5-11.
Oyaizu et al., "Role of Apoptosis in HIV Disease Pathogenesis", J. of Clinical Immunology, vol. 15, No. 5, 1995, pp. 217-231.
Paku, S., "Origin and Structural Evolution of the Early Proliferating Oval Cells in Rat Liver", American Journal of Pathology, vol. 158, No. 4, Apr. 2001, pp. 1313-1323.
Palmer et al., "Telomere Length, Telomerase Activity, and Replicative Potential in HIV Infection: Analysis of CD4+ and CD8+ T Cells from HIV-discordant Monozygotic Twins", J. Experimental Medicine, vol. 185, No. 7, 1997, pp. 1381-1386.
Panteleo, Giuseppe, "Unraveling the Strands of HIV's Web", Nature Medicine, vol. 5, No. 1, 1999, pp. 27-28.
Papageorgopoulos et al., "Measuring Protein Synthesis by Mass Isotopomer Distribution Analysis (MIDA)", Analytical Biochemistry, vol. 267, 1999, pp. 1-16.
Papageorgopoulos et al., "Toward the Measurement of Protein Synthesis by Mass Isotopomer Distribution Analysis (MIDA):Resolution of Isotopomers in a [d.sub.3 ]—Leucine Enriched Synthetic Oligopeptide Using Electrospray/Quadrupole Mass Spectrometry (ESI/MS)", Abstract, Federation of American Societies for Experimental Biology, vol. 1022, 1993, p. A177.
Park et al., "Measurement of Small Intestinal Cell Turnover with [6, 6, 2H2] Glucose", Berkeley Scientific, Abstract, vol. 1, No. 2, 1997, pp. 41-43.
Parks et al., "Carbohydrate-induced Hypertriacylglycerolemia: Historical Perspective and Review of Biological Mechanisms", Am. J. Nutr., vol. 71, 2000, pp. 412-433.
Parks et al., "Dependence of Plasma a-Tocopherol Flux on Very Low-Density Triglyceride Clearance in Humans", Free Radical Biology & Medicine, vol. 29, No. 11, 2000, pp. 1151-1159.
Parks et al., "Effects of a Low-Fat, High-Carbohydrate Diet on VLDL-Triglyceride Assembly, Production, and Clearance", J. Clin. Invest. vol. 104, No. 8, 1999, pp. 1087-1096.
Paša-Tolic et al., "High Throughput Proteome-Wide Precision Measurements of Protein expression Using Mass Spectrometry", J. Am. Chem. Soc., vol. 121, 1999, pp. 7949-7950.
Patsalos et al., "Pattern of Myelin Breakdown During Sciatic Nerve Wallerian Degeneration: Reversal of the Order of Assembly", The Journal of Cell Biology, vol. 87, 1980, pp. 1-5.
Patterson et al., "Concentration Dependence of Methyl-Palmitate Isotope Ratios by Electron Impact Ionization Gas Chromatography/Mass Spectrometry", Biol. Mass Spectrom., vol. 22, 1993, pp. 481-486.
Patterson et al., "Measurement of Very Low Stable Isotope Enrichments by Gas Chromatography/Mass Spectrometry: Application to Measurement of Muscle Protein Synthesis", Metabolism, vol. 46, No. 8, Aug. 1997, pp. 943-948.
Patton et al., "Measurements of Fatty Acid Synthesis by Incorporation of Deuterium from Deuterated Water", Biochemistry, vol. 18, No. 14, 1979, pp. 3186-3188.
Perelson et al., "Decay Characteristics of HIV-1-Infected Compartments During Combination Therapy", Nature 387, 1997, pp. 188-191.
Perelson et al., "HIV-1 Dynamics in Vivo: Virion Clearance Rate, Infected Cell Life-Span, and Viral Generation Time", Science, vol. 271, 1996, pp. 1582-1586.
Perochon et al., "Radiolabeling of the Lipids of Chinese Hamster Ovary Cells with the Probe [3-(Trifluoromethyl)-3-(m-[125]iodophenyl)diazirine", Analytical Biochemistry, vol. 254, 1997, pp. 109-118.
Picou et al., "The Measurement of Muscle Mass in Children Using [15N] Creatine", Pediatric Research, vol. 10, 1976, pp. 184-188.
Poortmans et al., "Estimation of Total-Body Skeletal Muscle Mass in Children and Adolescents", Medicine & Science in Sports & Exercise, vol. 37, 2005, pp. 316-322.
Pozharisski et al., "Study of Kinetics of Epithelial Cell Populations in Normal Tissues of the Rat's Intestines and in Carcinogenesis", Exp. Path., Bd., vol. 18, 1980, pp. 387-406.
Previs et al., "Estimation of Protein Turnover In Vivo Using D2O", Diabetes Abstract Book, 61st Scientific Sessions, vol. 50, Supplement 2, A301, Jun. 2001, p. A-301.
Previs et al., "A Critical Evaluation of Mass Isotopomer Distribution Analysis of Gluconeogenesis in Vivo", American Journal of Physiology—Endocrinology and Metabolism, vol. 277, No. 1, Jul. 1999, E154-E160.
Previs, Stephen F., "Application of Mass Isotopomer Distribution Analysis to Measurement of Gluconeogenesis and Glycerol Metabolism", Case Western University, May 1997, 360 pages.
Price et al., "Analysis of Proteome Dynamics in the Mouse Brain", PNAS, vol. 107, No. 32, Aug. 10, 2010, pp. 14508-14513.

(56) References Cited

OTHER PUBLICATIONS

Price et al., "Measurement of Human Plasma Proteome Dynamics with 2H2O and Liquid Chromatography Tandem Mass Spectrometry", Analytical Biochemistry, vol. 420, 2012, pp. 73-83.
Propper et al., "Use of Positron Emission Tomography in Pharmacokinetic Studies to Investigate Therapeutic Advantage in a Phase I Study of 120-Hour Intravenous Infusion XR5000", Journal of Clinical Oncology, vol. 21, No. 2, Jan. 2003, pp. 203-210.
Quehenberger et al., "The Human Plasma Lipidome", The New England Journal of Medicine, vol. 365, No. 19, Nov. 2011, pp. 1812-1823.
Quintao et al., "An Evaluation of four methods for measuring Cholesterol Absorption by the Intestine in Man", Journal of Lipid Research, vol. 12, 1971, pp. 221-232.
Radziuk, J., "Insulin Sensitivity and its Measurement: Structural Commonalities among the Methods", The Journal of Endocrinology & Metabolism, vol. 85, No. 12, Dec. 2000, pp. 4426-4433.
Ramakers et al., "Chronic Suppression of Bioelectric Activity and Cell Survival in Primary Cultures of Rat Cerebral Cortex Biochemical Observations", European Journal of Neuroscience, vol. 3, No. 2, 1991, pp. 154-161.
Ravichandran et al., "In Vivo Labeling Studies on the Biosynthesis and Degradation of Collagen in Experimental Myocardial Infarction", Biochemistry Journal, vol. 24, No. 3, 1991, pp. 405-414.
Reeds et al., "Muscle Mass and Composition in Malnourished Infants and Children and Changes Seen after Recovery", Pediatric Research, vol. 12, 1978, pp. 613-618.
Reichard, P., "From Deoxynucleotides to DNA Synthesis", Federation Proceedings, vol. 37, No. 1, 1978, pp. 9-14.
Reichard, P., "Interactions Between Deoxyribonucleotide and DNA Synthesis", Ann. Rev. Biochem. vol. 57, 1988, pp. 349-374.
Reindl et al., "Multivariate Analysis of a 3D Mass Spectral Image for Examining Tissue Heterogeneity", Integrative Biology (Camb), vol. 3, No. 4, Apr. 2011, pp. 460-467.
Reindl et al., "Rapid Screening of Fatty Acids using NanostructureInitiator Mass Spectrometry", Analytical chemistry, vol. 82, No. 9, 2010, pp. 3751-3755.
Reis-Filho et al., "Triple Negative Tumours: A Critical Review", Histopathology, vol. 52, 2008, pp. 108-118.
Rittenberg et al., "Deuterium as an Indicator in the Study of Intermediary Metabolism—VIII. Hydrogenation of Fatty Acids in the Animal Organism", Journal of Biological Chemistry, vol. 117, Feb. 1937, pp. 485-490.
Rittenberg et al., "Deuterium as an Indicator in the Study of Intermediary Metabolism—X. The Metabolism of Butyric and Caproic Acids", Journal of Biological Chemistry, vol. 120, Sep. 1937, pp. 503-510.
Rittler et al., "Effect of Tumor Removal on Mucosal Protein Synthesis in Patients with Colorectal Cancer", American Journal of Physiology-Endocrinology and Metabolism, vol. 284, 2003, pp. E1018-E1021.
Roberts, S. B., "Use of the Doubly Labeled Water Method for Measurement of Energy Expenditure, Total Body Water, Water Intake, and Metabolizable Energy Intake in Humans and Small Animals", Can. J. Physiol. Pharmacol., vol. 67, No. 10, 1989, pp. 1190-1198.
Robin et al., "Mitochondria DNA Molecules and Virtual Number of Mitochondria per Cell in Mammalian Cells", Journal of Cellular Physiology, vol. 136, 1988, pp. 507-513.
Robinson et al., "D20 to Determine Muscle Protein Synthesis Rates in Response to Post-Exercise Nutrition in Adults", Faseb Journal. Fed. of American Soc. for Experimental Biology, vol. 24, Apr. 2010, 1 page.
Robinson et al., "Long-Term Synthesis Rates of Skeletal Muscle DNA and Protein are Higher during Aerobic Training in Older Humans than in Sedentary Young Subjects but are not altered by Protein Supplementation", The FASEB Journal, vol. 25, No. 9, 2011, pp. 3240-3249.
Robosky, L. C., "In Vivo Toxicity Screening Programs Using Metabonomics", Combinatorial Chemistry & High Throughput Screening. vol. 5, 2002, pp. 651-662.
Rocha et al., "Accumulation of Bromodeoxyuridine-Labelled Cells in Central and Peripheral Lymphoid Organs: Minimal Estimates of Production and Turnover Rates of Mature Lymphocytes", Eur. J. Immunol., vol. 20, 1990, pp. 1697-1708.
Rockwood et al., "Rapid Calculation of Isotope Distributions", Analytical Chemistry, vol. 67, No. 15, 1995, pp. 2699-2704.
Rockwood et al., "Ultrahigh-Speed Calculation of Isotope Distributions", Analytical Chemistry, vol. 68, No. 13, 1996, pp. 2027-2030.
Rockwood et al., "Dissociation of Individual Isotopic Peaks: Predicting Isotopic Distributions of Product Ions in MSn", American Society for Mass Spectrometry, Jan. 18, 2003, pp. 311-322.
Roda et al., "Results with Six 'Kit' Radioimmunoassays for Primary Bile Acids in Human Serum Intercompared", Clin. Chem. vol. 26, No. 12, 1980, pp. 1677-1682.
Roddy et al., "Imaging of Freeze-Fractured Cells with in Situ Fluorescence and Time-of-Flight Secondary Ion Mass Spectrometry", Analytical Chemistry, vol. 74, No. 16, 2002, pp. 4011-4019.
Roederer, M., "T-Cell Dynamics of Immunodeficiency", Nature Medicine, vol. 1, No. 7, Jul. 1995, pp. 621-622.
Rooyackers et al., "Tracer Kinetics Are of Limited Value to Measure In Vivo Protein Synthesis and Degradation Rates in Muscle of Anesthetized Rats", Metabolism, vol. 45, No. 10, Oct. 1996, pp. 1279-1283.
Rosin et al., "The Use of Exfoliative Cell Samples to Map Clonal Genetic Alterations in the Oral Epithelium of High-Risk Patients", Cancer Research, vol. 57, Dec. 1, 1997, pp. 5258-5260.
Royale et al., "Techniques for Investigating Substrate Metabolism in Patients", Annals of the Royal College of Surgeons of England, vol. 63, 1981, pp. 415-419.
Safdar et al., "Global and Targeted Gene Expression and Protein Content in Skeletal Muscle of Young Men Following Short-Term Creatine Monohydrate Supplementation", Physiol Genomics, vol. 32, 2008, pp. 219-228.
Sakurai, Y., "The Meanings of Measuring Biological Metabolism Using a Stable Isotope Labeled Tracer: The Difference in Metabolism Between a Healthy Human and a Patient in Surgically Serious Condition", Medical Journal of Fukita Academy, vol. 20, No. 1, 1996, pp. 9-21.
Santarelli, L. et al., "Requirement of Hippocampal Neurogenesis for the behavioral effects of Antidepressants", Science, vol. 301, No. 5634, Aug. 8, 2003, pp. 805-809.
Sawada et al., "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver", Mutation Research, vol. 344, 1995, pp. 109-116.
Scalise, K., "Tracking T-Cells in AIDS Patients: A Safe Reliable Method of Measuring Human Cell Generation Rates", Berkeleyan, Feb. 11-17, 1998, 3 pages.
Scheibner et al., "Bile Acid Synthesis from Newly Synthesized Vs. Preformed Cholesterol Precursor Pools in the Rat", Hepatology, vol. 17, 1993, pp. 1095-1102.
Scheibner et al., "Complex Feedback Regulation of Bile Acid Synthesis in the Hamster: The Role of Newly Synthsized Cholesterol", Hepatology, vol. 30, 1999, pp. 230-237.
Schiller et al., "Matrix-Assisted Laser Desorption and Ionization Time-of-Flight (MALDITOF) Mass Spectrometry in Lipid and Phospholipid Research", Progress in Lipid Research, vol. 43, 2004, pp. 449-488.
Schneiter et al., "Kinetics of Dexamethasone Induced Alterations of Glucose Metabolism in Healthy Humans", American Journal of Physiology, 1998, pp. E806-E813.
Schoenheimer et al., "Deuterium as an Indicator in the Study of Intermediary Metabolism—III. The Role of the Fat Tissues", The Journal of Biological Chemistry, vol. 111, 1935, pp. 175-181.
Schoenheimer et al., "Deuterium as an Indicator in the Study of Intermediary Metabolism—IX. The Conversion of Stearic Acid into Palmitic Acid in the Organism", The Journal of Biological Chemistry, vol. 120, 1937, pp. 155-165.

(56) References Cited

OTHER PUBLICATIONS

Schoenheimer et al., "Deuterium as an Indicator in the Study of Intermediary Metabolism—V. The Desaturation of Fatty Acids in Organism", Journal of Biological Chemistry, vol. 113, Mar. 1936, pp. 505-510.

Schutte et al., "Total Plasma Creatinine: an Accurate Measure of Total Striated Muscle Mass", The American Physiological Society, vol. 51, No. 3, 1981, pp. 762-766.

Schwamborn et al., "R. M. Molecular Imaging by Mass Spectrometry-Looking Beyond Classical Histology", Nature Reviews Cancer, vol. 10, 2010, pp. 639-646.

Schwarz et al., "Short-Term Alterations in Carbohydrate Energy Intake in Humans", J. Clin. Invest., vol. 96, 1995, pp. 2735-2743.

Search Report received for European Patent Application No. 04812281.6, mailed on Oct. 6, 2010, 4 pages.

Seiler et al., "The Influence of Catabolic Reactions on Polyamine Excretion", Biochem. J., vol. 225, 1985, pp. 219-226.

Shen et al., "Purification of Oligodendrocyte and Its Myelination to the Demyelinated Culture Model in Vitro", ActaHistochem. Cytochem, vol. 35, No. 2, 2002, p. 123.

Shevchenko et al., "Rapid 'de Novo' Peptide Sequencing by a Combination of Nanoelectrospray, Isotopic Labeling and a Quadrupole/Time-of-flight Mass Spectrometer", Rapid Commun. Mass Spectrom., vol. 11, 1997, pp. 1015-1024.

Shigenaga et al., "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection", Methods in Enzymology, vol. 234, 1994, pp. 16-33.

Siler et al., "De Novo Lipogenesis, Lipid Kinetics, and Whole-Body Lipid Balances in Humans after Acute Alcohol Consumption1-3", American Journal of Clinical Nutrition, vol. 70, 1999, pp. 928-936.

Siler et al., "The Inhibition of Gluconeogenesis Following Alcohol in Humans", Am. J. Physiol., vol. 275, 1998, pp. E897-E907.

Siler et al., "VLDL-Triglyceride Production After Alcohol Ingestion, Studied Using [2-13C1] Glycerol", J. Lipid Res., vol. 39, 1998, pp. 2319-2328.

Smith et al., "The Phosphogluconate Odixative Pathway", in Principles of Biochemistry, 7th edition, McGraw-Hill Book Company., 1983, pp. 417-423.

Smith-Palmer, Truis, "Separation Methods Applicable to Urinary Creatine and Creatinine", Journal of Chromatography B, vol. 781, 2002, pp. 93-106.

Sosa-Peinado et al., "Overexpression and Biosynthetic Deuterium Enrichment of TEM-1 Beta-Lactamase for Structural Characterization by Magnetic Resonance Methods", Protein Expression and Purification, vol. 19, No. 2, Jul. 2000, pp. 235-245.

Spector et al., "Membrane Lipid Composition and Cellular Function", Journal of Lipid Research, vol. 26, 1985, pp. 1015-1035.

Sperling et al., "Quantitative Analysis of Isotope Distributions in Proteomic Mass Spectrometry Using Least-Squares Fourier Transform Convolution", Analytical Chemistry, vol. 80, No. 13, Jul. 1, 2008, pp. 4906-4917.

Sprent et al., "CD4+ Cell Turnover", Nature, vol. 375, 1995, 194 pages.

Stimpson et al., "Longitudinal Changes in Total Body Creatine Pool Size and Skeletal Muscle Mass using the D3-Creatine Dilution Method", Journal of Cachexia, Sarcopenia and Muscle, vol. 4, No. 3, Jun. 25, 2013, pp. 217-223.

Stimpson et al., "Longitudinal Determination of Total Body Creatine Pool Size and Skeletal Muscle Mass in Rats by D3-Creatine Dilution", The Faseb Journal, vol. 27, Apr. 1, 2013, p. lb410.

Stingl et al., "Characterization of Bipotent Mammary Epithelial Progenitor Cells in Normal Adult Human Breast Tissue", Breast Can Res and Treatment, vol. 67, 2001, pp. 93-109.

Stingl et al., "Purification and Unique Properties of Mammary Epithelial Stem Cells", Nature, vol. 439, Feb. 2006, pp. 993-997.

Sunter et al., "Cell Population Kinetics in the Epithelium of the Colon of the Male Rat", Virchows Archiv. B Cell Path., vol. 26, 1978, pp. 275-287.

Supplementary Partial European Search Report received for European Patent Application No. 03713429.3, mailed on Mar. 22, 2006, 7 pages.

Supplementary Partial Search Report Received for European Patent Application No. 02806603.3, mailed on Jul. 25, 2006, 5 pages.

Supplementary Partial Search Report received for European Patent Application No. 03749756.7, mailed on Aug. 17, 2005, 6 pages.

Supplementary Partial Search Report received for European Patent Application No. 03768624.3, mailed on Sep. 22, 2006, 4 pages.

Supplementary Search Report received for European Patent Application No. 04809469.2, mailed on Jul. 28, 2009, 5 pages.

Supplementary Search Report received for European Patent Application No. 05725448.4, mailed on Jun. 30, 2009, 7 pages.

Supplementary Search Report received for European Patent Application No. 05733311.4, mailed on Sep. 19, 2008, 9 pages.

Swinnen et al., "Increased Lipogenesis in Cancer Cells: New Players, Novel Targets", Current Opinion in Clinical Nutrition and Metabolic Care, vol. 9, 2006, pp. 358-365.

Szymanski et al., "Beyond the Proteome: Non-Coding Regulatory RNAs", Genome Biology, vol. 3, No. 5, Apr. 15, 2002, 8 pages.

Takats et al., "Mass Spectrometry Sampling under Ambient Conditions with Desorption Electrospray Ionization", Science, vol. 306, Oct. 15, 2004, pp. 471-473.

Tayek et al., "Glucose Production, Recycling, and Gluconeogenesis in Normals and Diabetics: A Mass Isotopomer [U_13C] Glucose Study", 1996, pp. E709-E717.

Teixeira et al., "Poor CD4 T Cell Restoration After Suppression of HIV-1 Replication May Reflect Lower Thymic Function", AIDS, vol. 15, No. 14, 2001, pp. 1749-1756.

Tennant et al., "Metabolic Transformation in Cancer", Carcinogenesis, vol. 30, No. 8, 2009, pp. 1269-1280.

Tint et al., "Transformation of 5α-cholest-7-en-3β-ol to Cholesterol and Cholestanol in Cerebrotendinous Xanthomatosis", Journal of Lipid Research, vol. 15, 1974, pp. 256-262.

Traber et al., "Isolation of Intestinal Epithelial Cells for the Study of Differential Gene Expression Along the Crypt-Villus Axis", Am. J. Physiol., vol. 260, 1991, pp. G895-G903.

Trappe et al., "Effect of Ibuprofen and Acetaminophen on Postexercise Muscle Protein Synthesis", Am J Physiol Endocronol Metab, vol. 282, 2002, pp. E551-E556.

Trere et al., "High Prevalence of Retinoblastoma Protein Loss in Triple-Negative Breast Cancers and its Association with a Good Prognosis in Patients Treated with Adjuvant Chemotherapy", Annals of Oncology, vol. 20, No. 11, Nov. 2009, pp. 1818-1823.

Turner et al., "Emerging Applications of Kinetic Biomarkers in Preclinical and Clinical Drug Development", Current Opinion in Drug Discovery & Development, vol. 8, No. 1, 2005, pp. 115-126.

Turner et al., "Measurement of Triglyceride (TG) synthesis and turnover in Vivo by 2H2O Incorporation into the Glycerol Moiety and Application of MIDA", Endocrinology and Metabolism, vol. 285, Oct. 2003, pp. E790-E803.

Turner et al., "Dissociation between Adipose Tissue Fluxes and Lipogenic Gene Expression in ob/ob Mice", American Journal of Physiology—Endocrinology and Metabolism, vol. 292, No. 4, Apr. 2007, pp. E1101-E1109.

Turner, S. M., "Stable Isotopes, Mass Spectrometry, and Molecular Fluxes: Applications to Toxicology", Journal of Pharmacological and Toxicological Methods, vol. 53, 2006, pp. 75-85.

Van Hinsbergh et al., "Palmitate Oxidation by Rat Skeletal Muscle Mitochondria", Archives of Biochemistry and Biophysics, vol. 190, No. 2, 1978, pp. 762-771.

Van Loan et al., "Monitoring Changes in Fat-Free Mass in HIV-Positive Men With Hypotestosteronemia and AIDS Wasting Syndrome Treated With Gonadal Hormone Replacement Therapy", AIDS, vol. 13, 1999, pp. 241-248.

Veenstra et al., "Proteome Analysis Using Selective Incorporation of Isotopically Labeled Amino Acids", J. Am. Soc. Mass. Spectrom. vol. 11, 2000, pp. 78-82.

(56) References Cited

OTHER PUBLICATIONS

Veerkamp et al., "14CO2 Production Is No Adequate Measure of [14C]Fatty Acid Oxidation", Biochemical Medicine and Metabolic Biology, vol. 35, 1986, pp. 248-259.
Véniant et al., "Defining the Atherogenicity of Large and Small Lipoproteins Containing Apolipoproteins B100", J. Clin. Invest. vol. 106, No. 12, 2000, pp. 1501-1510.
Viale et al., "Current Concepts on Hyperpolarized Molecules in MRI", Current Opinion in Chemical Biology, vol. 14, No. 1, 2010, pp. 90-96.
Wadke et al., "Fatty Acid Synthesis by Liver Perfused with Deuterated and Tritiated Water", Biochemistry, vol. 12, No. 14, 1973, pp. 2619-2624.
Wain-Hobson, S., "Virological Mayhem", Nature, vol. 373, 1995, 102 pages.
Waldeman et al., "A Comparison Between Bromodeoxyuridine and 3 H Thymidine Labeling in Human Breast Tumors", Modern Path, vol. 4, No. 6, 1991, pp. 718-722.
Wang et al., "Effects of Nicotinic Acid on Fatty Acid Kinetics, Fuel Selection, and Pathways of Glucose Production in Women", Am. J. Physiol. Endocrinol. Metab., vol. 279, 2000, pp. E50-E59.
Wang et al., "Total-Body Skeletal muscle Mass: Evaluation of 24-h Urinary Creatinine Excretion by Computerized Axial Tomography", American Society for Clinical Nutrition, vol. 63, 1996, pp. 863-869.
Wang et al., "Urinary Creatinine-Skeletal Muscle Mass Method: A Prediction Equation Based on Computerized Axial Tomography1-3", Biomedical and Environmental Sciences, vol. 9, 1996, pp. 185-190.
Wang et al., "Validation of a Single-Isotope-Labeled Cholesterol Tracer Approach for Measuring Human Cholesterol Absorption", Lipids, vol. 39, No. 1, 2004, pp. 87-91.
Waterlow, J. C., "Protein Turnover in the Whole Animal", Invest. Cell Pathol. vol. 3, 1980, pp. 107-119.
Watt et al., "Skeletal Muscle Total Creatine Content and Creatine Transporter Gene Expression in Vegetarians Prior to and Following Creatine Supplementation", International Journal of Sport Nutrition and Exercise Metabolism, vol. 14, No. 5, Oct. 2004, pp. 517-531.
Wei et al., "Viral Dynamics in Human Immunodeficiency Virus Type 1 Infection", Nature, vol. 373, 1995, pp. 117-122.
Weigelt et al., "Breast Cancer Metastasis: Markers and Models", Nature Reviews, Cancer, vol. 5, Aug. 2005, pp. 591-602.
Welle et al., "Utility of Creatinine Excretion in Body-Composition Studies of Healthy Man and Women Older than 60 y1-3", The American Journal of Clinical Nutrition, vol. 63, Feb. 1996, pp. 151-156.
Wells et al., "Body Composition by 2H Dilution in Gambian Infants: Comparison with UK Infants and Evaluation of Simple Prediction Methods", The British Journal of Nutrition, vol. 102, 2009, pp. 1776-1782.
Whittmann et al., "Application of MALDI-TOF MS to lysine-producing Corynebacterium glutamicum: a novel approach for metabolic flux analysis", Eur. J. Biochem, vol. 268, 2001, pp. 2441-2455.
Winett et al., "Exercise Regimens for Men With HIV", JAMA, vol. 284, No. 2, 2000, pp. 175-176.
Winograd et al., "Improvements in SIMS continue is the end in Sight?", Applied Surface Science, vol. 252, No. 19, 2006, pp. 6836-6843.
Wiseman et al., "Desorption Electrospray Ionization Mass Spectrometry: Imaging Drugs and Metabolites in Tissues", PNAS, vol. 105, No. 47, Nov. 25, 2008, pp. 18120-18125.
Wolf, George, "The Effect of Fasting and Fructose and Glucose Infusion on Gluconeogenesis and Triose Phosphate Flux in Rats in Vivo", Nutrition Reviews, vol. 53, No. 10, 1995, pp. 299-302.
Wolfe et al., "Glucose Metabolism in Humans", ACS Symposium Series 258, Chapter 12, Turnund et al. ed., 1984, pp. 175-189.
Wolfe, Robert R., "Isotopic Measurement of Glucose and Lactate Kinetics", Ann. Med., vol. 22, 1990, pp. 163-170.
Wolthers et al., "Rapid CD4+ T-Cell Turnover in HIV-1 Infection: a Paradigm Revisited", Immunol. Today, vol. 19, No. 1, 1998, pp. 44-48.
Wolthers et al., "T Cell Telomere Length in HIV-1 Infection: No Evidence for Increased CD4+ T Cell Turnover", Science, vol. 274, 1996, pp. 1543-1547.
Wong et al., "From Monoamines to Genomic Targets: A Paradigm Shift for Drug Discovery in Depression", Nature Reviews Drug Discovery, vol. 3, Feb. 2004, pp. 136-151.
Wood et al., "Estimation of Pathways of Carbohydrate Metabolism", Biochemische Zeitschrift, vol. 338, 1963, pp. 809-847.
Written Opinion mailed Jul. 14, 2006, by the Australian Patent Office for Singapore Patent Application No. 200502593-7, filed Nov. 4, 2003, 5 pages.
Written Opinion received for PCT Patent Application No. PCT/US2004/021063 mailed on Apr. 4, 2005, 3 pages.
Yanes et al., "Nanostructure Initiator Mass Spectrometry: Tissue Imaging and Direct Biofluid Analysis", Anal Chem., vol. 81, No. 8, Apr. 2009, pp. 2969-2975.
Yecies et al., "Transcriptional Control of Cellular Metabolism by mTOR Signaling", Cancer Research, vol. 71, No. 8, Apr. 15, 2011, pp. 2815-2820.
Yoshimura et al., "Real-Time Analysis of Living Animals by Electrospray Ionization Mass Spectrometry", Anal Biochemistry, vol. 417, No. 2, Oct. 2011, pp. 195-201.
Zeisel, Steven H., "Choline: An Essential Nutrient for Humans", Nutrition, vol. 16, No. 7/8, 2000, pp. 669-671.
Zhang et al., "Deuterium NMR Study of the Origin of Hydrogen in Fatty Acids Produced In Vivo in Chicken", European Journal of Lipid Science and Technology, vol. 108, 2006, pp. 125-133.
Zhang et al., "Kinetics of CD4+ T Cell Repopulation of Lymphoid Tissues after Treatment of HIV-1 Infection", Proc. Natl. Acad. Sci. USA, vol. 95, Feb. 1998, pp. 1154-1159.
Zilversmit et al., "On the Calculation of 'Turnover Time' and 'Turnover Rate' from Experiments Involving the Use of Labeling Agents", J. of General Physiology, vol. 26, No. 3, 1943, pp. 325-331.

\* cited by examiner

FIGURE 1
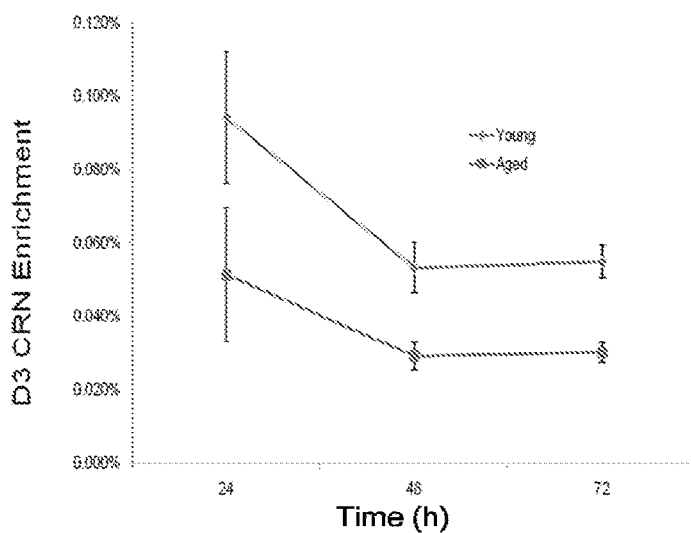
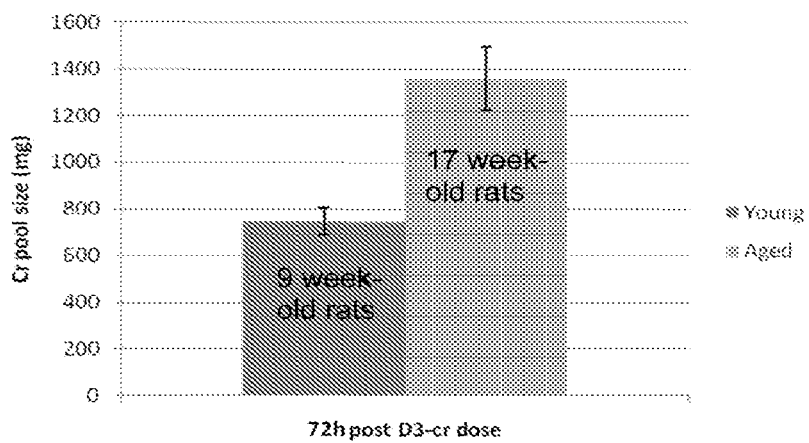

METHODS FOR DETERMINING TOTAL BODY SKELETAL MUSCLE MASS

CROSS REFERENCE TO RELATED APPLICATIONS

This application is a continuation of U.S. patent application Ser. No. 14/363,779, now abandoned, which is a U.S. National Phase Patent Application under 35 U.S.C. §371 based on International Application No. PCT/US2012/068068, filed Dec. 6, 2012, which claims the benefit under 35 U.S.C. §119(e) of U.S. Provisional Application No. 61/567,952, filed Dec. 7, 2011, and U.S. Provisional Application No. 61/708,013, filed Sep. 30, 2012, the disclosures of which are hereby incorporated by reference in their entirety.

FIELD OF THE INVENTION

This invention relates to methods for determining the total body pool size of creatine and total body skeletal muscle mass in a subject by the use of an orally administered tracer dose of D3-creatine, and encompasses improved methods for determining the concentration of creatinine in a biological sample.

BACKGROUND OF THE INVENTION

Skeletal muscle plays a central role in metabolic adaptations to increasing and decreasing physical activity, in disease (e.g. cachexia), in obesity, and in aging (e.g. sarcopenia). Sarcopenia is described as the age-associated loss of skeletal muscle (Evans (1995) *J. Gerontol.* 50A:5-8) and has been associated with mobility disability (Janssen and Ross, (2005) *J. Nutr. Health Aging* 9:408-19) and greatly increased health-care costs for elderly people (Janssen et al. (2004) *J. Am. Geriatr. Soc.* 52:80-5). Loss of skeletal muscle with advancing age is associated with decreased energy requirements and concomitant increase in body fatness, weakness and disability, insulin resistance and risk of diabetes. Loss of skeletal muscle associated with an underlying illness (cachexia) is associated with a greatly increased mortality (Evans (2008) *Clin. Nutr.* 27:793-9).

Because of the important role total body skeletal muscle mass plays in aging and disease, there is an effort in the pharmaceutical arts to identify therapeutic agents that will stimulate muscle protein synthesis and increase muscle mass. However, current methodologies for quantification of muscle synthesis and muscle mass often involve invasive procedures (e.g. muscle biopsies) or rely on expensive equipment (i.e. DEXA, MRI, or CT) that provides only indirect data on whole body muscle mass. Because of these limitations, no method is routinely used in the clinic for estimation of skeletal muscle mass, and no diagnostic criteria for estimates of muscle mass have been produced. As a result, there is a no straightforward way to determine the effects of potential therapeutic agents on muscle protein synthesis mass.

Accordingly, there remains a need in the art for reliable, easily-performed, non-invasive measurements of total body skeletal muscle mass.

BRIEF SUMMARY OF INVENTION

The present invention is based on the finding that steady-state enrichment of D3-creatinine in a urine sample following oral administration of a single defined tracer dose of D3-creatine can be used to calculate total-body creatine pool size and skeletal muscle mass in a subject.

The invention is further based on the finding that the concentration of creatinine in a biological sample can be determined by measuring the concentration of creatinine M+2 isotope and dividing this concentration by a dilution factor, where the dilution factor is the ratio of the concentration of creatinine M+2 to the concentration of creatinine M+0 in the biological sample. Determining the creatinine concentration in a biological sample according to these improved methods allows for the simultaneous measurement of the concentration of creatinine and D3-creatinine in a single sample using widely-available instrumentation. Accordingly, this improved detection method will facilitate the wide-spread adaptation of the present methods for use in determining skeletal muscle mass in patients.

Accordingly, in one aspect the invention provides a method for determining the total body skeletal muscle mass in a subject, where the method comprises the steps of:
- (a) orally administering 10-200 mg D3-creatine or a salt or hydrate thereof to the subject;
- (b) allowing at least 12 hours to elapse after the administration of the D3-creatine;
- (c) obtaining a biological sample from the subject,
- (d) determining the concentration of creatinine and D3-creatinine in said biological sample;
- (e) using the creatinine and D3-creatinine concentrations determined in step
- (f) to calculate the total body skeletal muscle mass of the subject.

In particular embodiments, the biological sample is a urine sample.

In certain embodiments, the concentration of creatinine and D3-creatinine in the urine sample is determined by HPLC/MS/MS.

In another aspect, the invention provides a method of determining the concentration of creatinine in a biological sample from a subject, said method comprising the steps of:
- (a) obtaining a biological sample from the subject;
- (b) analyzing the biological sample to determine the peak area of the creatinine M+2 isotope peak for the biological sample;
- (c) comparing the peak area determined in step (b) to a calibration curve generated using D3-creatinine to determine the concentration of the creatinine M+2 isotope in the biological sample;
- (d) dividing the concentration obtained in step (c) by a dilution factor, where the dilution factor is the ratio of the concentration of creatinine M+2 to the concentration of creatinine M+0 in the biological sample.

BRIEF DESCRIPTION OF THE DRAWINGS

FIG. 1. Urinary D3-creatinine enrichment and total body creatine pool size in growing rats. (A) Urinary D3-creatinine enrichment (determined by isotope ratio mass spectrometry) in 9 week-old (mean body weight 304±11 g, n=10) and 17 week-old (mean body weight 553±39 g, n=10) rats at the indicated time after a single oral 0.475 mg dose of D3-creatine, showing achievement of isotopic steady state by 48 h, and clear separation of growing rat age groups (P<0.001 between groups at all times; within groups, the difference between 48 and 72 h is not significant; 2-factor ANOVA and Student's t test). (B) Creatine pool size calculated from 72 h urinary D3-creatinine enrichments for the rat groups in FIG. 1, showing clear separation of age groups (p<0.0001).

DETAILED DESCRIPTION OF THE INVENTION

Figure 2:
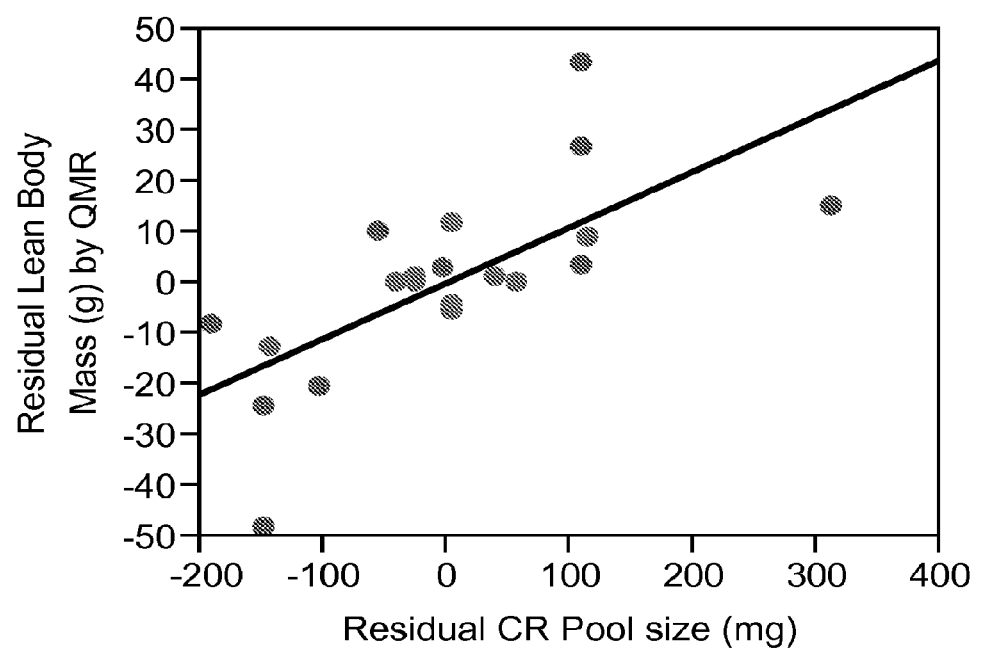
FIG. 2. Correlation between Lean Body Mass by Quantitative Magnetic Resonance and total body creatine pool size, adjusted for age effect, for the rat groups in FIG. 1 ($r_{all\ rats}$=0.69; P<0.001).

The present invention is based on the finding that enrichment of D3-creatinine in a urine sample following oral administration of a single defined dose of D3-creatine can be used to calculate total-body creatine pool size and skeletal muscle mass in a subject. Accordingly, the invention provides a non-invasive, accurate method of determining total body skeletal muscle. The methods of the invention find use, inter alia, in diagnosing and monitoring medical conditions associated with changes in total body skeletal muscle mass, and in screening potential therapeutic agents to determine their effects on muscle mass.

According to the method, D3-creatine is orally administered to a subject. Although the present is not limited by mechanism, it is believed that the D3-creatine is rapidly absorbed, distributed, and actively transported into skeletal muscle, where it is diluted in the skeletal muscle pool of creatine. Skeletal muscle contains the vast majority (>than 98%) of total-body creatine. In muscle tissue, creatine is converted to creatinine by an irreversible, non-enzymatic reaction at a stable rate of about 1.7% per day. This creatinine is a stable metabolite that rapidly diffuses from muscle, is not a substrate for the creatine transporter and cannot be transported back into muscle, and is excreted in urine. As a result, once an isotopic steady-state is reached, the enrichment of a D3-creatinine in spot urine sample after a defined oral tracer dose of a D3 creatine reflects muscle creatine enrichment and can be used to directly determine creatine pool size. Skeletal muscle mass can then be calculated based on known muscle creatine content.

Accordingly, in one aspect the invention provides a method of determining the total body skeletal muscle mass in a subject, where the method comprises the steps of:
(a) orally administering 10-200 mg D3-creatine or a salt or hydrate thereof to the subject;
(b) allowing at least 12 hours to elapse after the administration of the D3-creatine;
(c) obtaining a urine sample from the subject,
(d) determining the concentration of creatinine and D3-creatinine in said urine sample;
(e) using the creatinine and D3-creatinine concentrations determined in step
(f) to calculate the total body skeletal muscle mass of the subject.

In certain embodiments, a hydrate of D3-creatine is administered to the subject. In particular embodiments, D3-creatine monohydrate is administered.

The dose of D3-creatine to be administered to the subject is preferably selected such that the labeled creatine is rapidly absorbed into the bloodstream and spillage of excess label into the urine is minimized. Accordingly, for a human subject the dose of D3-creatine is typically 5-250 mgs, such as 20-125 mgs. In particular embodiments, 5, 10, 20, 30, 40, 50, 60, 70, 80, 90, or 100 mgs of D3-creatine is administered. In some embodiments, the dose is adjusted based on the gender of the subject. Thus, in certain embodiments, the subject is female and 10-50, such as 20-40, or more particularly, 30 mg of D3-creatine is administered to the subject. In other embodiments, the subject is male and 40-80 mg, such as 50-70, or more particularly, 60 mg or 70 mg of D3-creatine is administered to the subject.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component may be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents may also be present.

Capsules can be made by preparing a powder, liquid, or suspension mixture and encapsulating with gelatin or some other appropriate shell material. Glidants and lubricants such as colloidal silica, talc, magnesium stearate, calcium stearate, or solid polyethylene glycol may be added to the mixture before the encapsulation. A disintegrating or solubilizing agent such as agar-agar, calcium carbonate or sodium carbonate may also be added to improve the availability of the medicament when the capsule is ingested. Moreover, when desired or necessary, suitable binders, lubricants, disintegrating agents, and coloring agents may also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets can be formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture may be wet-granulated with a binder such as syrup, starch paste, acadia mucilage or solutions of cellulosic or polymeric materials, and forcing through a screen. As an alternative to granulating, the powder mixture may be run through the tablet machine and the result is imperfectly formed slugs broken into granules. The granules may be lubricated to prevent sticking to the tablet forming dies by means of the addition of stearic acid, a stearate salt, talc or mineral oil. The lubricated mixture is then compressed into tablets. The compounds of the present invention may also be combined with a free flowing inert carrier and compressed into tablets directly without going through the granulating or slugging steps. A clear or opaque protective coating consisting of a sealing coat of shellac, a coating of sugar or polymeric material, and a polish coating of wax may be provided. Dyestuffs may be added to these coatings to distinguish different unit dosages.

Oral fluids such as solutions, syrups, and elixirs may be prepared in dosage unit form so that a given quantity contains a predetermined amount of the compound. Syrups may be prepared, for example, by dissolving the compound in a suitably flavored aqueous solution, while elixirs are prepared through the use of a non-toxic alcoholic vehicle. Suspensions may be formulated generally by dispersing the compound in a non-toxic vehicle. Solubilizers and emulsifiers such as ethoxylated isostearyl alcohols and polyoxy ethylene sorbitol ethers may be added. Solubilizers that may be used according to the present invention include Cremophor EL, vitamin E, PEG, and Solutol. Preservatives and/or flavor additives such as peppermint oil, or natural sweeteners, saccharin, or other artificial sweeteners; and the like may also be added.

According to the method, the urine sample in preferably collected after enrichment levels of D3-creatinine in the urine have reached a steady-state. Thus in one embodiment, at least 6 hours or at least 12 hours is allowed to elapse after the administration of the D3-creatine but prior to the collection of the urine sample. In certain embodiments, at least 24 hours is allowed to elapse. In particular embodiments, at least 36 hours, at least 48 hours, at least 60 hours, or at least 72 hours are allowed to elapse after the administration of the D3-creatine and before the collection of the urine sample.

The invention also encompasses certain improved analytic methods for detecting creatinine and D3-creatinine in urine samples. Specifically, the invention provides for the detection of creatinine and D3-creatinine in urine samples by HPLC/MS, particularly HPLC/MS/MS. However, alternate methods know in the art may also be used to detect creatinine and/or D3 creatinine in urine samples. Such methods include direct or indirect colorimetric measurements, the Jaffe method, enzymatic degradation analysis, or derivatization of the creatinine followed by GC/MS analysis of HPLC with fluorescence detection.

Thus in one aspect, the invention provides a method of determining the concentration of creatinine in a biological sample from a subject, said method comprising the steps of:
 (a) obtaining a biological sample from the subject;
 (b) analyzing the biological sample to determine the peak area of the creatinine M+2 isotope peak for the biological sample;
 (c) comparing the peak area determined in step (b) to a calibration curve generated using D3-creatinine to determine the concentration of the creatinine M+2 isotope in the biological sample;
 (d) dividing the concentration obtained in step (c) by a dilution factor, where the dilution factor is the ratio of the concentration of creatinine M+2 to the concentration of creatinine M+0 in the biological sample.

The biological sample may be any appropriate sample including, but not limited to, urine, blood, serum, plasma, or tissue. In one particular embodiment, the biological sample is a urine sample. In another particular embodiment, the biological sample is a blood sample.

In a preferred embodiment, the peak area of the creatinine M+2 isotope peak is determined using liquid chromatography/mass spectroscopy (LC/MS/MS).

In one embodiment, the dilution factor is 0.0002142±0.0000214. More particularly, the dilution factor is 0.0002142±0.00001, such as 0.0002142±0.000005.

The methods of the invention are useful for diagnosing and monitoring medical conditions associated with changes in total body skeletal muscle mass. Examples of medical conditions in which loss of muscle mass plays an important role in function, performance status, or survival include, but are not limited to frailty and sarcopenia in the elderly; cachexia (e.g., associated with cancer, chronic obstructive pulmonary disease (COPD), heart failure, HIV-infection, tuberculosis, end stage renal disease (ESRD); muscle wasting associated with HIV therapy, disorders involving mobility disability (e.g., arthritis, chronic lung disease); neuromuscular diseases (e.g., stroke, amyotrophic lateral sclerosis); rehabilitation after trauma, surgery (including hip-replacement surgery), medical illnesses or other conditions requiring bed-rest; recovery from catabolic illnesses such as infectious or neoplastic conditions; metabolic or hormonal disorders (e.g., diabetes mellitus, hypogonadal states, thyroid disease); response to medications (e.g., glucocorticoids, thyroid hormone); malnutrition or voluntary weight loss. The claimed methods are also useful in sports-related assessments of total body skeletal muscle mass.

The methods of the invention are also useful for screening test compounds to identify therapeutic compounds that increase total body skeletal muscle mass. According to this embodiment, the total body skeletal mass of a subject is measured according to the method before and after a test compound is administered to the subject.

The assessment of total body skeletal muscle mass can be repeated at appropriate intervals to monitor the effect of the test compound on total body skeletal muscle mass.

EXPERIMENTAL

Use of the D3-Creatine Tracer Dilution Method to Determine Total Body Skeletal Muscle Mass in a Pre-Clinical Model A dose of 0.475 mg D3-creatine per rat was determined to be rapidly and completely absorbed and reach the systemic circulation with minimal urinary spillage, such that >99% of the D3-creatine tracer dose should be available to equilibrate with the body creatine pool.

The creatine dilution method was then used to determine urinary D3-creatine enrichment and the time to isotopic steady state in growing rats. In a cross-sectional study, a single oral dose of 0.475 mg D3-creatine per rat was given to two groups of rats, 9 and 17 weeks of age, and urine was collected at 24, 48, and 72 hour time points after dosing. As expected, the larger, older rats had lower urinary D3-creatinine enrichment (expressed as mole percent excess, MPE) at all time points than the younger, smaller rats, reflecting greater dilution of the D3-creatine tracer in the total body creatine pool. For both age groups, urinary enrichment was highest at 24 h and stable between 48 and 72 h, indicating isotopic steady state was achieved between 24 and 48 h after the tracer D3-creatine dose. (FIG. 1A).

Total body creatine pool size was then calculated using a formula for determination of pool size based on enrichment of a tracer, assuming a single creatine pool (Wolfe and Chinkes (2005) Calculation of substrate kinetics: Single-pool model. 2nd ed. *Isotope tracers in metabolic research*. Hoboken, N.J.: John Wiley & Sons, Inc. 21-9): the D3-creatine dose (0.475 mg) was divided by the D3-creatinine enrichment (MPE/100). FIG. 1B shows the total body creatine pool sizes calculated from urinary enrichment 72h after the tracer dose for the 9 and 17 week-old rat groups and indicates the creatine pool size for the larger, older rats is significantly larger than for the smaller, younger rats.

Figure 3:
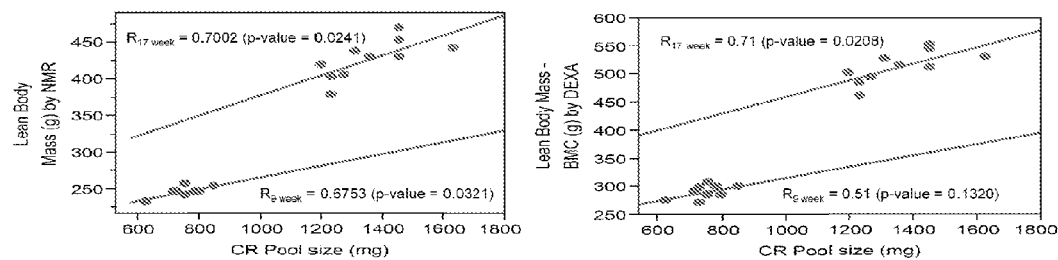
FIG. 3. Even within the rat groups of different age from FIG. 1, there is a significant correlation of creatine pool size and lean body mass by either quantitative magnetic resonance (left) or DEXA (right).

The day before giving the tracer dose of D3-creatine, lean body mass (LBM) in all rats was assessed by either quantitative magnetic resonance (QMR) or DEXA. FIG. 2 shows that after accounting for age effect, LBM by QMR and creatine pool size are significantly correlated. LBM by QMR and creatine pool size are also significantly correlated within each age group, and LBM by DEXA and creatine pool size are significantly correlated within the 17 week-old age group (FIG. 3).

In a second cross-sectional study, an older rat age group (still within the rat growth phase of 22 weeks of age) was treated once daily subcutaneously with either saline vehicle, or dexamethasone to induce skeletal muscle atrophy for 2 weeks prior the administration of D3-creatine. As with the first cross-sectional study with 9 and 17 week-old rats, isotopic steady state was reached between 48 and 72 h.

Figure 4:
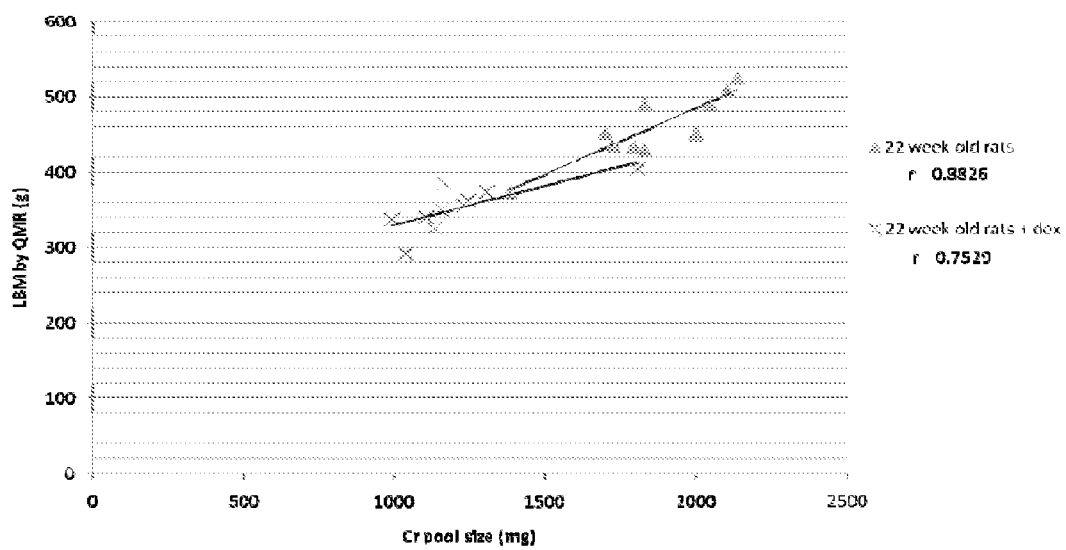
FIG. 4. Significant correlation between lean body mass determined by quantitative magnetic resonance and creatine pool size determined by D3-creatine dilution in 22 week-old rats (n=10 per group) treated the previous two weeks with either vehicle or dexamethasone (P<0.001 and P=0.01, respectively).

Compared to vehicle-treated controls, dexamethasone induced a significant reduction in LBM (353±32 vs. 459±45 g, P<0.001) and a significant reduction in total body creatine pool size (1216±227 vs. 1853±228 mg, P<0.001). As in the first study, LBM and creatine pool size were significantly correlated within the two individual treatment groups (FIG. 4).

Figure 5:
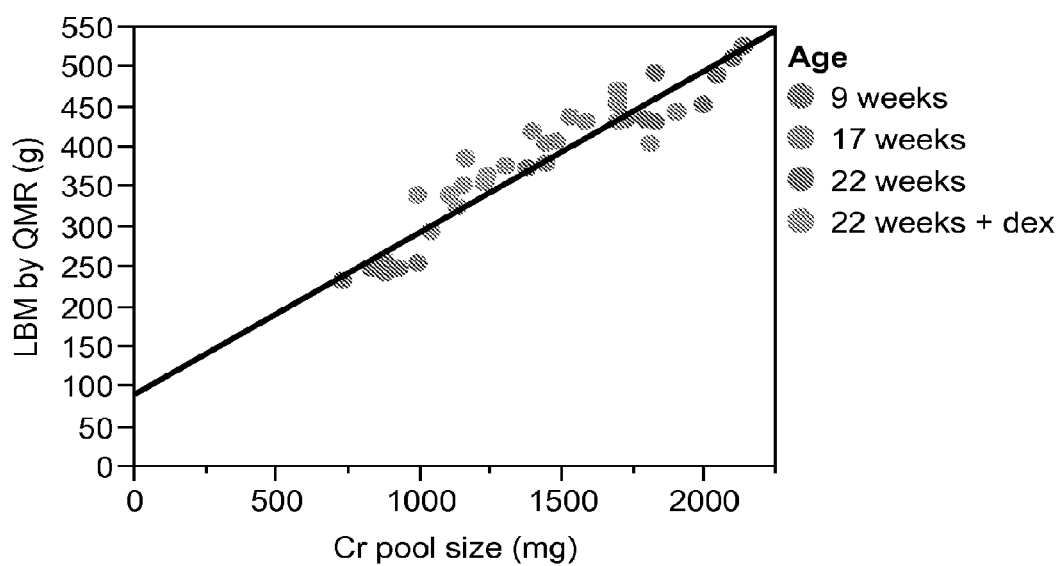
FIG. 5. Correlation between lean body mass determined by quantitative magnetic resonance and total-body creatine pool size determined by D3-creatine dilution for all 40 rats used in the two cross-sectional studies (y=0.20x+91.6; r=0.9517; P<0.0001).
Figure 6:
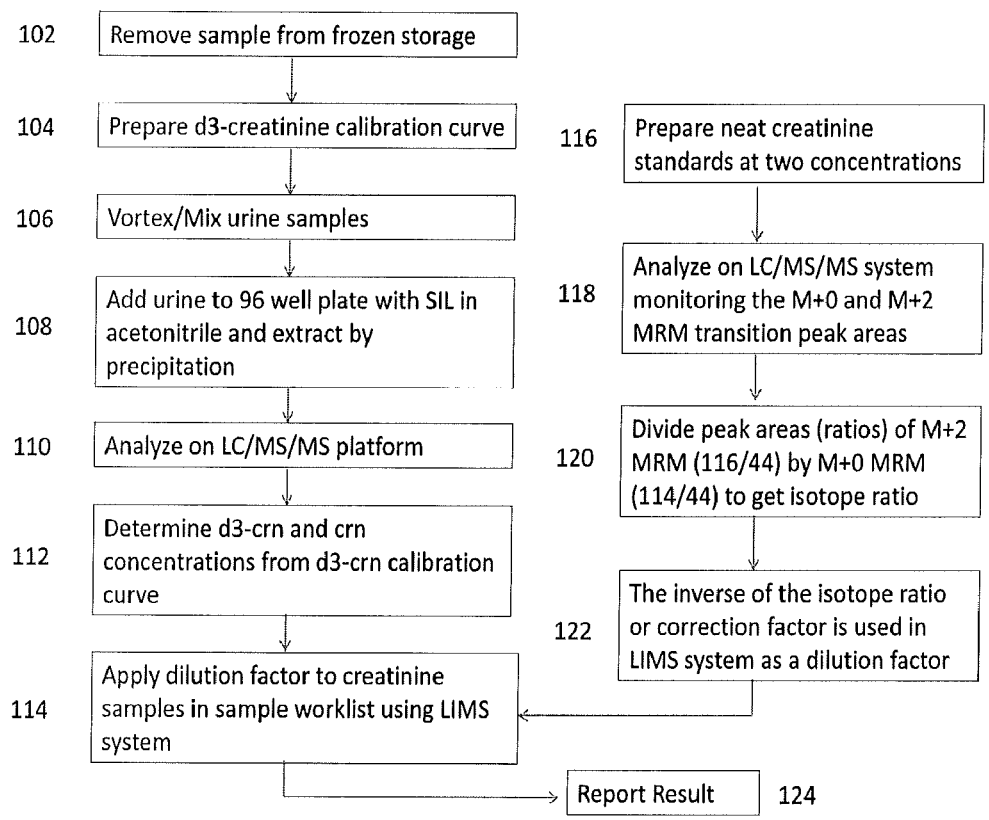
FIG. 6. This figure shows a flow chart for one embodiment of the method of determining total body skeletal mass.

FIG. 5 show the correlation between LBM and creatine pool size for all 40 rats used in the two cross-sectional studies (r=0.95; P<0.001).

Use of the D3-Creatine Tracer Dilution Method to Determine Total Body Skeletal Muscle Mass in Human Subjects Human subjects are orally administered a single dose of 30, 60, or 100 mgs of D3 creatine-monohydrate. Urine samples are then collected 1, 2, 3, 4, 5, or 6 days after administration of the D3-creatine monohydrate dose.

Urine pharmacokinetic analyses for each collection interval may include quantitation of MPE ratio by IRMS, ratio of deuterium-labeled creatine+deuterium-labeled creatinine to total creatine+total creatinine by LCMS, total creatinine, creatine pool size, and % of deuterium-labeled creatine dose excreted in urine.

Steady-state enrichment (MPE) can be assessed both visually and from the estimate of the slope from the linear regression of enrichment (MPE) vs time (midpoint of each urine collection interval). A mixed effect ANOVA model can be fit with time (continuous variable) as a fixed effect and subject as a random effect. The coefficient for the slope of the time effect can be used to evaluate steady-state. The 90% confidence intervals for the slope can be calculated.

Creatine pool size can be estimated once steady-state enrichment has been achieved a for each collection interval during steady-state according to the formula:

[Amount of $D3$ Cr dosed (g)–total Amount of urinary $D3$ Cr$(0-t)$ (g)]/enrichment ratio$(t)$ where t is the urine collection interval during steady-state.

Muscle mass can be estimated from the creatine pool size by assuming that the creatine concentration is 4.3 g/kg of whole wet muscle mass (WWM) (Kreisberg (1970) *J Appl Physiol* 28:264-7).

Muscle mass=creatine pool size/Cr concentration in muscle

Creatine pool size can also be estimated by total urine creatinine (moles/day) divided by K (1/day).

The excretion rate constant (K) can be estimated using a rate excretion method by estimating the declining slope of the line for the log of the amount of D3-creatine in urine collection interval vs. time (midpoint of that urine collection interval) for each collection interval over time. This estimate of K can be used in calculating creatine pool size from 24 hr urinary creatinine excretion rather than using an estimate of turnover form the literature.

Analytic Methods for Quantitating D3-Creatine and D3-Creatinine in Urine Samples from Clinical Subjects Reference Standards of D3-Creatine monohydrate and D3-creatinine were purchased from C/D/N Isotopes, Montreal Canada.

HPLC-MS/MS Analysis

The separation of D3-creatine was carried out using an Acquity UPLC (Waters Corp., Milford, Ma.) equipped with a Zorbax Hilic Plus silica analytical column (50×2.1 mm, Rapid Resolution HD 1.8μ, Agilent Corp., Santa Clara Calif.). Injection volume is typically 8 μL.

Mobile phase A (MP A) consisted of 10 mM ammonium formate in water and mobile phase B is acetonitrile. Gradient chromatography was employed with initial mobile phase composition of 2% 10 mM ammonium formate with a flow rate of 0.7 mL/min. This was held for 0.5 minute and then a linear gradient to 50% MPA was achieved at 2.3 minutes. This was immediately increased to 80% and held for 0.4 minutes and then returned to starting conditions at 2.9 minutes. The total run time was 3.5 minutes. This gradient allowed baseline separation of the D3-creatine from interfering compounds.

The detection of D3-creatine was carried out using a Sciex API5000 (Applied Biosystems, Foster City, Calif.). The HPLC system was connected to the API5000 through a turbo ion spray source operating in positive ionization mode using the following parameters: ionization temperature of 650° C., ionspray voltage of 2500 V, curtain gas setting of 45 ($N_2$), nebulizer gas setting was 65 ($N_2$), drying gas setting was 70 ($N_2$), collision gas setting of 3 ($N_2$). All other mass spectrometer parameters were optimized for the individual transitions. The following ion transitions (MRM) were acquired: D3-creatine is m/z=135 to m/z=47 with a typical retention time of 1.99 min. The creatine standard is monitored with an ion transition of m/z=139 to m/z=50 with a typical retention time of 1.99 min.

The separation of the creatinine and D3-creatinine analytes were carried out using an Acquity UPLC (Waters Corp., Milford, Ma.) equipped with a Zorbax Hilic Plus silica analytical column, dimensions of 50×2.1 mm (Rapid Resolution HD 1.8μ, Agilent Corp., Santa Clara Calif.). Injection volume was typically 5 μL.

Mobile phase A consisted of 5 mM ammonium formate and mobile phase B was acetonitrile. Gradient chromatography was employed with initial mobile phase composition of 2% 5 mM ammonium formate with a flow rate of 0.7 mL/min. This was held for 0.4 minute and then a linear gradient to 40% MPA was achieved at 2.1 minutes. This was immediately increased to 50% at 2.2 minutes and held for 0.4 minutes and then returned to starting conditions at 2.7 minutes. The total run time was 3.5 minutes. This gradient allowed baseline separation of the d3-creatinine and creatinine from interfering compounds.

The detection of the creatinine and D3-creatinine analytes was carried out using a Sciex API5000 (Applied Biosystems, Foster City, Ca.). The HPLC system was connected to the API5000 through a turbo ion spray source operating in positive ionization mode using the following parameters: ionization temperature of 350° C., ionspray voltage of 5500 V, curtain gas setting of 45 ($N_2$), nebulizer gas setting was 60 ($N_2$), drying gas setting was 65 ($N_2$), collision gas setting of 3 ($N_2$). All other mass spectrometer parameters were optimized for the individual transitions. The following ion transitions (MRM) were acquired: D3-creatinine is m/z=117 to m/z=47 and for creatinine (M+2 isotope) was m/z=116 to m/z=44 with a typical retention time of 1.5 min. The creatine standard is monitored with an ion transition of m/z=121 to m/z=51 with a typical retention time of 1.5 min. For creatinine, the M+2 isotope version was acquired to avoid diluting the sample with buffer.

Endogenous creatinine concentration values are determined in human urine clinical samples using a D3-creatinine calibration standard curve. The D3-creatinine isotope behaves similarly to creatinine throughout the extraction and HPLC-MS/MS procedures, thus allowing clean urine matrix to prepare standards and QC samples.

The amount of endogenous creatinine (m/z=114) in the human clinical samples is much greater ~(1000 fold) than the levels of D3-creatinine. Therefore, instead of diluting the sample, the M+2 isotope of creatinine (m/z=116) will be monitored, thus allowing the simultaneous measurement of creatinine and D3-creatinine from one sample analysis. The MRM of (M+2) endogenous creatinine (116/44) is monitored. A correction factor that represents the ratio of the MRM of 116/44 to 114/44, is used to correct the calculated concentrations determined from the d3-creatinine calibration curve. The isotope ratio (M+2) MRM/(M+0) MRM or correction factor is 0.00286. Therefore, the amount of D3-creatinine, which would come from the D3 creatine dose and the endogenous creatinine, can be quantitated from the single D3-creatinine calibration curve.

Example

Chemical and Reagents: Acetonitrile and Water (all HPLC grade or better) purchased from Sigma Aldrich (St. Louis, Mo.). Ammonium Formate purchased from Sigma Aldrich (St. Louis, Mo.). Reference Standards of d3-Creatine (monohydrate) and d3-creatinine were purchased from CDN Isotopes, Montreal Canada.

Stock solutions of d3-creatine and d3-creatinine are prepared at 1.0 mg/mL in water and confirmation of equivalence is performed. Dilute solutions ranging from 0.1 μg/mL to 100 μg/mL and 0.2 μg/mL to 200 μg/mL are prepared in water and used to prepare calibration standards and quality control (QC) samples in human urine for d3-creatine and d3-creatinine, respectively. Isotopically labelled internal standards for creatine (SIL) ($^{13}C_3{}^2H_3{}^{15}N_1$-creatine) and creatinine (SIL) ($^{13}C_3{}^2H_4{}^{15}N_1$-creatinine) are prepared at 1.0 mg/mL in water. Dilute solutions of these are prepared at 500 ng/mL in acetonitrile and used as an extraction solvent for the urine standards, quality controls and study samples.

Sample Preparation: (d3-creatine, creatinine and d3-creatinine in urine) A 200 μL aliquot of the internal standard working solution (500 ng/mL) in acetonitrile is added to each well, except double blank samples, acetonitrile is added. A 40 μL aliquot of sample, standard or QC is transferred to the appropriate wells in the plate containing the SIL. The plate is sealed and vortex mixed for approximately 3 minutes. The plate is centrifuged at approximately 3000 g for 5 minutes. Supernatant is transferred to a clean 96 well plate and then injected onto the HPLC-MS/MS system for analysis. D3-creatine and d3-creatinine are analyzed from separate human urine samples.

HPLC-MS/MS Analysis

The separation of d3-creatine, d3-creatinine and creatinine is carried out using an Acquity UPLC (Waters Corp., Milford, Ma.) equipped with a Agilent Zorbax Hilic Plus silica analytical column, dimensions of 50×2.1 mm (Rapid Resolution HD 1.8μ, Agilent Corp., Santa Clara Calif.). Injection volume is typically 2 μL.

D3-creatine: mobile phase A consists of 10 mM ammonium formate and mobile phase B is acetonitrile. Gradient chromatography is employed with initial mobile phase composition at 2% 10 mM ammonium formate with a flow rate of 0.7 mL/min. This is held for 0.5 minute and then a linear gradient to 50% MPA is achieved at 2.3 minutes. This is increased to 80% over 0.2 minutes and held for 0.4 minutes and then returned to starting conditions at 3.0 minutes. The total run time is 3.5 minutes.

The detection of d3-creatine is carried out using a Sciex API5000 (Applied Biosystems, Foster City, Ca.). The HPLC system is connected to the API5000 through a turbo ion spray source operating in positive ionization mode using the following parameters: ionization temperature of 650° C., ionspray voltage of 2500 V, curtain gas setting of 45 ($N_2$), nebulizer gas setting is 65 ($N_2$), drying gas setting is 70 ($N_2$), collision gas setting of 3 ($N_2$). All other mass spectrometer parameters are optimized for the individual transitions. The following ion transitions (MRM) are acquired: d3-creatine is m/z=135 to m/z=47 with a typical retention time of 2 min. The SIL is monitored with an ion transition of m/z=139 to m/z=50 with a typical retention time of 2 min. D3-creatinine: mobile phase A consisted of 5 mM ammonium formate, and mobile phase B is acetonitrile. Gradient chromatography is employed with initial mobile phase composition at 2% 5 mM ammonium formate with a flow rate of 0.7 mL/min. This is held for 0.4 minute and then a linear gradient to 60% acetonitrile is achieved at 2.1 minutes. This is immediately increased to 50% acetonitrile and held for 0.4 minutes and then returned to starting conditions at 2.7 minutes. The total run time is 3.5 minutes. The detection of the creatinine and d3-creatinine analytes is carried out using a Sciex API5000 (Applied Biosystems, Foster City, Ca.). The HPLC system was connected to the API5000 through a turbo ion spray source operating in positive ionization mode using the following parameters: ionization temperature of 350° C., ionspray voltage of 5500 V, curtain gas setting of 45 ($N_2$), nebulizer gas setting was 60 ($N_2$), drying gas setting was 65 ($N_2$), collision gas setting of 3 ($N_2$). All other mass spectrometer parameters are optimized for the individual transitions. The following ion transitions (MRM) are acquired: d3-creatinine is m/z=117 to m/z=47 and for creatinine (M+2 isotope) is m/z=116 to m/z=44 with a typical retention time of 1.5 min. The SIL is monitored with an ion transition of m/z=121 to m/z=51 with a typical retention time of 1.5 min. For creatinine, the M+2 isotope MRM is acquired to avoid diluting the sample with a surrogate matrix (a creatinine free control urine is not available). These isotopes will behave similarly throughout the extraction and HPLC-MS/MS procedures, thus allowing clean urine matrix to prepare standards and QC samples as well as allowing for the quantification of endogenous creatinine using a calibration curve that was generated from the deuterated form of creatinine. Therefore, the amount of d3-creatinine and the endogenous creatinine, can be quantitated from the single d3-creatinine calibration curve.

HPLC-MS/MS data were acquired and processed (integrated) using Analyst™ software (Version 1.4.2, MDS Sciex, Canada). A calibration plot of area ratio versus d3-creatinine concentration was constructed and a weighted $1/x^2$ linear regression applied to the data.

Results

To perform bioanalytical quantification of biomarkers using LC/MS/MS, a surrogate matrix or a surrogate analyte must be used. In this assay, human urine can be used since d3-creatinine is not found endogenously and the quantification of creatinine can be determined from the d3-creatinine calibration curve. The equivalency of d3-creatinine and creatinine is shown.

D3-Creatinine and Creatinine Equivalence Determination

A number of experiments were performed in order to verify that d3 creatinine can be used as a surrogate analyte to quantitate creatinine and that the MRM transition of 116/44 (M+2) can be used with the isotope ratio correction factor.

To confirm that d3 creatinine can be used as a surrogate analyte for creatinine; two concentration levels of creatinine and d3 creatinine neat standard solutions were prepared to show equivalent LC-MS/MS response. The peak areas of 200 ng/mL and 40 ng/mL of both creatinine and d3 creatinine standard solutions were compared using the MRM transitions of 114/44 and 117/47, respectively. The results showed that the two solutions gave equivalent responses with mean percent difference and percent CV of less than 7.5%. See Table 1.

TABLE 1

D3 creatinine and creatinine equivalence using LC/MS/MS

| Std (ng/mL) | d3-Creatinine (MRM of 117/44) | Creatinine (MRM of 114/44) | CRN vs d3 CRN % difference | Percent of D3 Response |
|---|---|---|---|---|
| 40 | 791648 | 717010 | 10.4 | 90.6 |
| 40 | 804513 | 780182 | 3.1 | 97.0 |
| 40 | 774228 | 717528 | 7.9 | 92.7 |
| 40 | 776144 | 823064 | −5.7 | 106.0 |
| 40 | 766927 | 828642 | −7.4 | 108.0 |
| 40 | 741290 | 758937 | −2.3 | 102.4 |
| | | Mean | 1.0 | 99.4 |
| | | % CV | | 7.2 |

| Std (ng/mL) | d3-Creatinine (MRM of 117/47) | Creatinine (MRM of 114/44) | CRN vs d3 CRN % difference | Percent of D3 Response |
|---|---|---|---|---|
| 200 | 3296195 | 3336107 | −1.2 | 101.2 |
| 200 | 3469440 | 3325274 | 4.3 | 95.8 |
| 200 | 3416181 | 3428709 | −0.4 | 100.4 |
| 200 | 3363696 | 3185389 | 5.6 | 94.7 |
| 200 | 3335259 | 3390463 | −1.6 | 101.7 |
| 200 | 3255799 | 3321365 | −2.0 | 102.0 |
| | | Mean | 0.8 | 99.3 |
| | | % CV | | 3.2 |

These results show that d3 creatinine and creatinine give equivalent LC/MS/MS responses and d3-creatinine can be used as a surrogate analyte for creatinine. This is not surprising since deuterated compounds are used routinely as stable label internal standards, in regulated environments to validate assays. These deuterated standards have been shown to correct LC/MS/MS response of analyte from matrix effects as well as other extraction and chromatographic related effects. Since the only difference is an extra proton at three hydrogen atoms on the methyl group, we would expect the two compounds to behave almost identically throughout the extraction, chromatographic separation and mass spectral detection.

Determination of Isotope Ratio

This method is used to determine the amount of d3 creatinine in human urine that has been converted from a dose of d3 creatine. Additionally, the amount of endogenous creatinine will be determined using the d3 creatinine standard curve. The amount of endogenous creatinine is much greater (~1000 fold) than the levels of d3-creatinine in the human clinical urine samples, therefore instead of diluting the sample, the M+2 isotope of creatinine will be monitored. This will allow the simultaneous measurement of creatinine and d3-creatinine from one sample using a urine matrix calibration curve. The peak area of the MRM of (M+2) endogenous creatinine (116/44) is monitored along with the d3 creatinine MRM of 117/47. A correction factor that represents the ratio of the MRM of 116/44 to 114/44, is used to correct the calculated concentrations determined from the d3-creatinine calibration curve.

The isotope ratio (response ratio) or difference in peak area response from the naturally abundant form of creatinine (M+0) or m/z=114 to the much less abundant form of creatinine (M+2) or m/z=116 is calculated experimentally. The isotope ratio is determined using two different experimental procedures. The original experimental design uses one standard concentration, a 200 ng/mL creatinine solution (Table 2a). The peak area of the creatinine is monitored at both the M+0 and M+2 MRM transitions (114/44 and 116/44), respectively. One solution was used to reduce variation which may occur from separate injections and preparation of separate solutions. This concentration is chosen because it allows the peak area of both MRMs to be in the detector range, and with adequate signal to noise for the smaller peak. However, some variability in the day to day measurements is observed (±10%) as shown in Table 3. Therefore, an additional experiment to generate this response ratio was performed. In the second approach, the response ratio is experimentally determined using two separate solutions. A separate solution for each MRM transition is prepared which gives peak areas that are closer in magnitude to each other. A 10 ng/mL solution of creatinine is used to acquire the MRM transition of 114/44 and a 500 ng/mL solution is used to acquire the MRM transition of 116/44. These solutions are injected on the LC/MS/MS system in replicates of 10 and the mean peak area ratio (PAR) for each solution is determined. The response ratio is then calculated by dividing the mean PAR of 116/44 by the corrected PAR of 114/44. In order to compare the PARs from the two MRMs, the PAR from the 10 ng/mL solutions is multiplied by 50 (since 500 ng/mL is 50 times larger than the 10 ng/mL), an example is shown in Table 2b. This allows the peak area of both solutions to be closer in value and potentially eliminating errors associated with integrating peaks with vastly different signal to noise values.

TABLE 2

Creatinine Response Ratio (M +2/M +0) Determination using LC/MS/MS

2a. Determined using a single creatinine standard solution

| STD (ng/mL) | Peak Area Ratio | | Response Ratio |
|---|---|---|---|
| | Creatinine (M + 2) MRM of 116/44 | Creatinine (M + 0) MRM of 114/44 | |
| 200 | 0.0209 | 9.19 | 0.00227 |
| 200 | 0.0216 | 9.42 | 0.00229 |
| 200 | 0.0195 | 9.53 | 0.00205 |
| 200 | 0.0208 | 9.42 | 0.00221 |

TABLE 2-continued

Creatinine Response Ratio (M +2/M +0) Determination using LC/MS/MS

| | | | |
|---|---|---|---|
| 200 | 0.0202 | 9.37 | 0.00216 |
| 200 | 0.0199 | 9.46 | 0.00210 |
| 200 | 0.0188 | 9.22 | 0.00204 |
| 200 | 0.0201 | 9.64 | 0.00209 |
| 200 | 0.0202 | 9.33 | 0.00217 |
| 200 | 0.0188 | 9.49 | 0.00198 |
| 200 | 0.0200 | 9.45 | 0.00212 |
| 200 | 0.0198 | 9.32 | 0.00212 |
| Mean | 0.0201 | 9.4 | 0.00213 |
| % CV | 4.05 | 1.35 | 3.10 |

2b. Determined using separate creatinine concentrations

Peak Area Ratio

| | Creatinine (M + 2) MRM of 116/44 | Creatinine (M + 0) MRM of 114/44 | Creatinine (M + 0)* MRM of 114/44 | Response Ratio |
|---|---|---|---|---|
| | 0.0460 | 0.4240 | 21.2 | 0.00217 |
| | 0.0467 | 0.4240 | 21.2 | 0.00220 |
| | 0.0466 | 0.3990 | 20.0 | 0.00234 |
| | 0.0471 | 0.4110 | 20.6 | 0.00229 |
| | 0.0477 | 0.4000 | 20.0 | 0.00239 |
| | 0.0459 | 0.3850 | 19.3 | 0.00238 |
| | 0.0453 | 0.3990 | 20.0 | 0.00227 |
| | 0.0452 | 0.4000 | 20.0 | 0.00226 |
| | 0.0443 | 0.3920 | 19.6 | 0.00226 |
| | 0.0442 | 0.3780 | 18.9 | 0.00234 |
| Mean | 0.0459 | 0.4 | 20.1 | 0.00229 |
| % CV | 2.53 | 3.75 | 3.75 | 3.15 |

*= corrected for concentration difference

The corrected peak area ratio would be equivalent to a 500 ng/mL creatinine standard monitoring the peak area of the MRM transition of 114/44.

The isotope ratio (response ratio) was determined on multiple occasions over a four month time span and on two different triple quadrapole instruments. The mean of these nine values was determined and the inverse of this response ratio is the dilution factor used to correct the creatinine values in the LIMS system. See Table 3.

TABLE 3

Summary of Response Ratio (M + 2/M + 0) Determined using LC/MS/MS

| | Date | Response Ratio | Instrument Name |
|---|---|---|---|
| | 22-Nov-11 | 0.00206 | RTP12 |
| | 29-Nov-11 | 0.00213 | RTP12 |
| AM | 7-Dec-11 | 0.00193 | RTP12 |
| PM | 7-Dec-11 | 0.00193 | RTP12 |
| * | 14-Jan-12 | 0.00221 | RTP12 |
| * | 16-Jan-12 | 0.00229 | RTP12 |
| * | 17-Jan-12 | 0.00195 | RTP12 |
| * | 7-Feb-12 | 0.00229 | RTP12 |
| * | 10-Feb-12 | 0.00249 | RTP52 |
| | Mean | 0.002142 | |
| | % CV | 9.09 | |

* = performed using two concentrations of creatinine

This experimentally determined response ratio is used to correct peak areas of creatinine M+2 (MRM of 116/44) and these corrected peak areas of creatinine were compared to peak areas run for the same concentration of d3 creatinine standard (MRM of 117/47). The comparison of the corrected creatinine peak area to the peak area obtained from the d3 creatinine standards gave equivalent responses with percent difference and percent CV of less than 10%. See Table 4.

TABLE 4

Creatinine (M + 2) Response Corrected using Response Ratio

| STD (ng/mL) | CRN (MRM 116/44) M + 2 | CRN M + 2* Corrected as to M + 0 | d3 CRN (MRM 117/47) Peak Area | Percent Difference |
|---|---|---|---|---|
| 200 | 7856.2 | 3667693.7 | 3599411.5 | 98.1 |
| 200 | 7422.7 | 3465312.8 | 3682013.9 | 106.3 |
| 200 | 6101.3 | 2848412.7 | 3516609.5 | 123.5 |
| 200 | 7490.2 | 3496825.4 | 3330922.4 | 95.3 |
| 200 | 7288.0 | 3402427.6 | 3359823.2 | 98.7 |
| 200 | 6625.6 | 3093183.9 | 3264518.6 | 105.5 |
| Mean | 7130.7 | 3328976.0 | 3458883.2 | 104.6 |
| % CV | 9.0 | 9.0 | 4.8 | 9.8 |

*= corrected peak area (divided by the mean response ratio of 0.002142)

That which is claimed:

1. A method of determining total body skeletal muscle mass in a subject, comprising:
   (a) orally administering $D_3$-creatine to a subject, wherein the $D_3$-creatine dilutes in the total body skeletal muscle pool of creatine and reaches isotopic steady-state in the total body skeletal muscle pool of creatine;
   (b) obtaining a biological sample comprising creatinine and $D_3$-creatinine from the subject, wherein the biological sample is a urine sample;
   (c) detecting creatinine and $D_3$-creatinine in the biological sample by a method selected from the group consisting of HPLC/MS, HPLC/MS/MS, LCMS, LC/MS/MS, and isotope ratio mass spectrometry (IRMS);
   (d) measuring enrichment ratio of $D_3$-creatinine in the biological sample at a time t based on the creatinine and $D_3$-creatinine detected in (c);
   (e) measuring a total amount of urinary $D_3$-creatinine from administration of the $D_3$-creatine to the time t;
   (f) determining total-body creatine pool size in the subject by the formula $$\frac{[\text{Amount of } D_3\text{-creatine dosed (g)} - \text{Total amount of urinary } D_3\text{-creatine } (o-t)(g)]}{\text{enrichment ratio } (t)} = \text{total-body creatine pool size;}$$

and
   (g) determining total body skeletal muscle mass in the subject based on the formula $$\text{Total body skeletal muscle mass} = \left(\frac{\text{the total-body creatine pool size}}{\text{creatine concentration in skeletal muscle}}\right).$$

2. The method of claim 1, wherein 5-250 mg $D_3$-creatine or a salt or hydrate thereof are administered.

3. The method of claim 1, wherein the $D_3$-creatine administered is a hydrate of $D_3$-creatine.

4. The method of claim 3, wherein the $D_3$-creatine is $D_3$-creatine monohydrate.

5. The method of claim 1, wherein the biological sample is obtained at least 24 hours after administration of the $D_3$-creatine.

6. The method of claim 5, wherein the biological sample is obtained at least 36 hours after administration of the $D_3$-creatine.

7. The method of claim 5, wherein the biological sample is obtained at least 48 hours after administration of the $D_3$-creatine.

8. The method of claim 5, wherein the biological sample is obtained at least 60 hours after administration of the $D_3$-creatine.

9. The method of claim 5, wherein the biological sample is obtained at least 72 hours after administration of the $D_3$-creatine.

10. The method of claim 1, wherein the $D_3$-creatine is administered to the subject such that spillage of $D_3$-creatine into the urine is minimized, wherein greater than 99% of the administered $D_3$-creatine dilutes in the total body skeletal muscle pool of creatine and reaches isotopic steady-state in the total body skeletal muscle pool of creatine.

11. The method of claim 1, wherein the creatine concentration in skeletal muscle is 4.3 g/kg.

\* \* \* \* \*

UNITED STATES PATENT AND TRADEMARK OFFICE
CERTIFICATE OF CORRECTION

PATENT NO. : 9,737,260 B2
APPLICATION NO. : 15/098217
DATED : August 22, 2017
INVENTOR(S) : Marc K. Hellerstein and William Evans Page 1 of 1

It is certified that error appears in the above-identified patent and that said Letters Patent is hereby corrected as shown below:

In the Claims

At Column 14, Claim number 1, Line numbers 34-35, please replace "(e) measuring a total amount of urinary $D_3$-creatinine from administration of the $D_3$-creatine to the time t;" with --(e) measuring a total amount of urinary $D_3$-creatine from administration of the $D_3$-creatine to the time t;--.

Signed and Sealed this
Twenty-second Day of October, 2019

Andrei Iancu
*Director of the United States Patent and Trademark Office*